(12) United States Patent
Blatt et al.

(10) Patent No.: US 7,476,548 B2
(45) Date of Patent: Jan. 13, 2009

(54) DRY REAGENT STRIP CONFIGURATION, COMPOSITION AND METHOD FOR MULTIPLE ANALYTE DETERMINATION

(75) Inventors: Joel M. Blatt, Mountain View, CA (US); Wilma M. Mangan, Santa Clara, CA (US)

(73) Assignee: Bayer Healthcare LLC, Tarrytown, NY (US)

( * ) Notice: Subject to any disclaimer, the term of this patent is extended or adjusted under 35 U.S.C. 154(b) by 552 days.

(21) Appl. No.: 10/816,230

(22) Filed: Mar. 31, 2004

(65) Prior Publication Data
US 2005/0130293 A1   Jun. 16, 2005

Related U.S. Application Data

(63) Continuation of application No. 09/298,358, filed on Apr. 23, 1999, now abandoned.

(60) Provisional application No. 60/082,786, filed on Apr. 23, 1998.

(51) Int. Cl.
*G01N 33/558* (2006.01)

(52) U.S. Cl. .............. 436/514; 422/55; 422/56; 422/57; 422/58; 435/287.1; 435/287.2; 435/287.7; 435/287.8; 435/287.9; 435/288.5; 435/805; 435/810; 435/970; 435/973; 436/169; 436/518; 436/530; 436/810

(58) Field of Classification Search .............. 422/55, 422/56, 57, 58; 435/287.1, 287.2, 287.7, 435/287.8, 287.9, 288.5, 805, 810, 970, 973; 436/169, 514, 518, 530, 810
See application file for complete search history.

(56) References Cited

U.S. PATENT DOCUMENTS

| | | | | |
|---|---|---|---|---|
| 5,354,692 A | * | 10/1994 | Yang et al. | 436/514 |
| 5,559,041 A | * | 9/1996 | Kang et al. | 436/518 |
| 5,707,818 A | * | 1/1998 | Chudzik et al. | 435/7.93 |
| 5,837,546 A | * | 11/1998 | Allen et al. | 436/169 |
| 5,945,345 A | * | 8/1999 | Blatt et al. | 436/518 |

FOREIGN PATENT DOCUMENTS

WO  88 08534  * 11/1988

OTHER PUBLICATIONS

Pradella et al., Clin. Chem. 36:1994-1995 (1990).
Daviaud et al., Clin. Chem. 39:53-59 (1993).

* cited by examiner

*Primary Examiner*—Christopher L Chin
(74) *Attorney, Agent, or Firm*—Lerner, David, Littenberg, Krumholz & Mentlik LLP

(57) ABSTRACT

An assay device, analytical instrument and assay method for determining the presence or amount of an analyte in a fluid is disclosed. The device is a one-step lateral flow dry reagent immunoassay with one, two or more zones along a transverse axis of the device, each zone can contain or be preceded by diffusively or non-diffusively bound reagents. The invention measures an indicator in one or two test zones for each analyte to determine its presence or concentration. The signal reagent (indicator) may be a particle such as a colored latex or colloidal gold. The assay quantitation may be read by an instrument.

27 Claims, 14 Drawing Sheets

Side View

Top View

DRY REAGENT STRIP CONFIGURATION, COMPOSITION AND METHOD FOR MULTIPLE ANALYTE DETERMINATION

CROSS REFERENCE TO RELATED APPLICATIONS

This application is a continuation of patent application U.S. Ser. No. 09/298,358, filed on Apr. 23, 1999, now abandonded, which claims priority to provisional patent application U.S. Ser. No. 60/082,786 filed on Apr. 23, 1998. The subject matter of this application is also related to patent application U.S. Ser. No. 08/512,844, filed on Aug. 9, 1995; patent application U.S. Ser. No. 08/703,479, which published as PCT 98/09167 on Mar. 5, 1998; and patent application U.S. Ser. No. 08/642,228, which published as PCT 97/41421 on Nov. 6, 1997. All such patents and applications are incorporated herein by reference in their entirety.

FIELD OF THE INVENTION

The present invention relates to a dry reagent assay device having two or more test zones, which provides for the simultaneous assay of multiple analytes in transverse, fluid communication with one another through a common, lateral flow transport matrix. More particularly, a single assay strip measures at least two different analytes and uses the measurement of one of the analytes to correct the net analytical result.

BACKGROUND OF THE INVENTION

Qualitative and quantitative self-tests have developed gradually over the last half century. Non-instrumented tests have become commercially available using immunochemical reagents on a solid support for diagnostic tests involving HCG, LH, FSH, CKMB, Staphylococcus, and Rubella. Measurement of the hormone HCG to detect pregnancy was among the first of these tests to become commercially successful in the home market. The first home pregnancy test, the e.p.t.™, was introduced in 1977 by Warner-Lambert. The e.p.t.™ used a solution phase chemical reaction that formed a brown ring on the surface of the urine solution in the presence of HCG. The 2 hour long protocol associated with this test was sensitive to vibration and timing, causing false results.

Two additional test systems that appeared in the late 1980s were the LipoScan™ by Home Diagnostics Inc. and the Chemcard™ by Chematics Inc. Both tests measure cholesterol in whole-blood using visual color comparison. Since visual color matching is subjective, these tests do not achieve the quantitative performance necessary for cholesterol testing (Pradella et al, Clin. Chem. 36:1994-1995 (1990)).

For many analytes such as the markers for pregnancy and ovulation, qualitative or semi-quantitative tests are appropriate. There are, however, a variety of analytes that require accurate quantitation. These include glucose, cholesterol, HDL cholesterol, triglyceride, a variety of therapeutic drugs such as theophylline, vitamin levels, and other health indicators. Generally, their quantitation has been achieved through the use of an instrument. Although suitable for clinical analysis, these methods are generally undesirable for point-of-care testing in physicians offices and in the home due to the expense of the instrument.

Recently, a number of non-instrumented methods for measuring analytes use instrument-free quantitation through the use of migration distance, rather than color matching, as the visual signal. In migration distance assays, chemical/biochemical reactions occur as the analyte is wicked through a solid support. During wicking the analyte reacts with a signal-producing reagent and forms a visible signal along the support. The migration distance or the distance of signal border is related to analyte concentration. The operator reads the height of the color bar much the same way one reads a thermometer, and finds the concentration from a calibrated scale. There are a few migration-type assays commercially available.

Although single use, thermometer-type, non-instrumented quantitative devices and non-instrumented color comparison devices for qualitative measurement have shown adequate performance, they have several problems associated with reliability and convenience. First, the colors generated on these devices are not always uniform and sharp. In the case of migration type assays the border is often light in color, unclear and difficult to read. This translates directly into user errors since the user must make a judgment related to the position of the color band border. In the case of non-instrumented pregnancy tests it is sometimes difficult to visually interpret the intensity of the colored spot (especially at HCG concentrations close to the cut-off sensitivity), and interpretation of the result is sometimes a problem. Anytime a non-technical operator is required to make a visual judgment or interpretation, an error is possible, and sometimes, is unavoidable.

Second, the assay protocol for these tests is sometimes difficult and lengthy, taking 15minutes to 1 hour to obtain a result. Third, these tests often do not have sufficient procedural and reagent references to assure adequate test performance. Fourth and last, non-instrumented devices can only measure single endpoint type tests since enzyme rates or ratiometric analysis of two analytes cannot be measured. Therefore, the menu of potential tests is limited. As an example of the significance of the problems, a recent article in Clinical Chemistry (Daviaud et al, Clin. Chem. 39:53-59 (1993)) evaluated all 27 home use pregnancy tests sold in France. The authors state, "among the 478 positive urine samples distributed, 230 were falsely interpreted as negative".

Thus, a need exists in the field of diagnostics for a wicking assay which is sufficiently accurate and reliable to permit point-of-care use by untrained individuals in locations such as the home, sites of medical emergencies, or locations other than a clinic.

SUMMARY OF THE INVENTION

According, it is an object of the present invention to provide a wicking device which uses competitive and immunoassay configurations for test results which are more accurate and reproducible than in the prior art.

It is a further object of the present invention to provide a assay method using multiple test zones in a single assay to yield accurate quantitative results.

Another object of the present invention is to provide an assay which provides means for quality reference using the signals combined from multiple test zones.

Other and further advantages, embodiments, variations and the like will be apparent to those skilled-in-the-art from the present specification taken with the accompanying drawings and appended claims.

BRIEF DESCRIPTION OF THE DRAWINGS

In the drawings, which comprise a portion of this disclosure.

DESCRIPTION OF THE PREFERRED EMBODIMENTS

Figure 1:
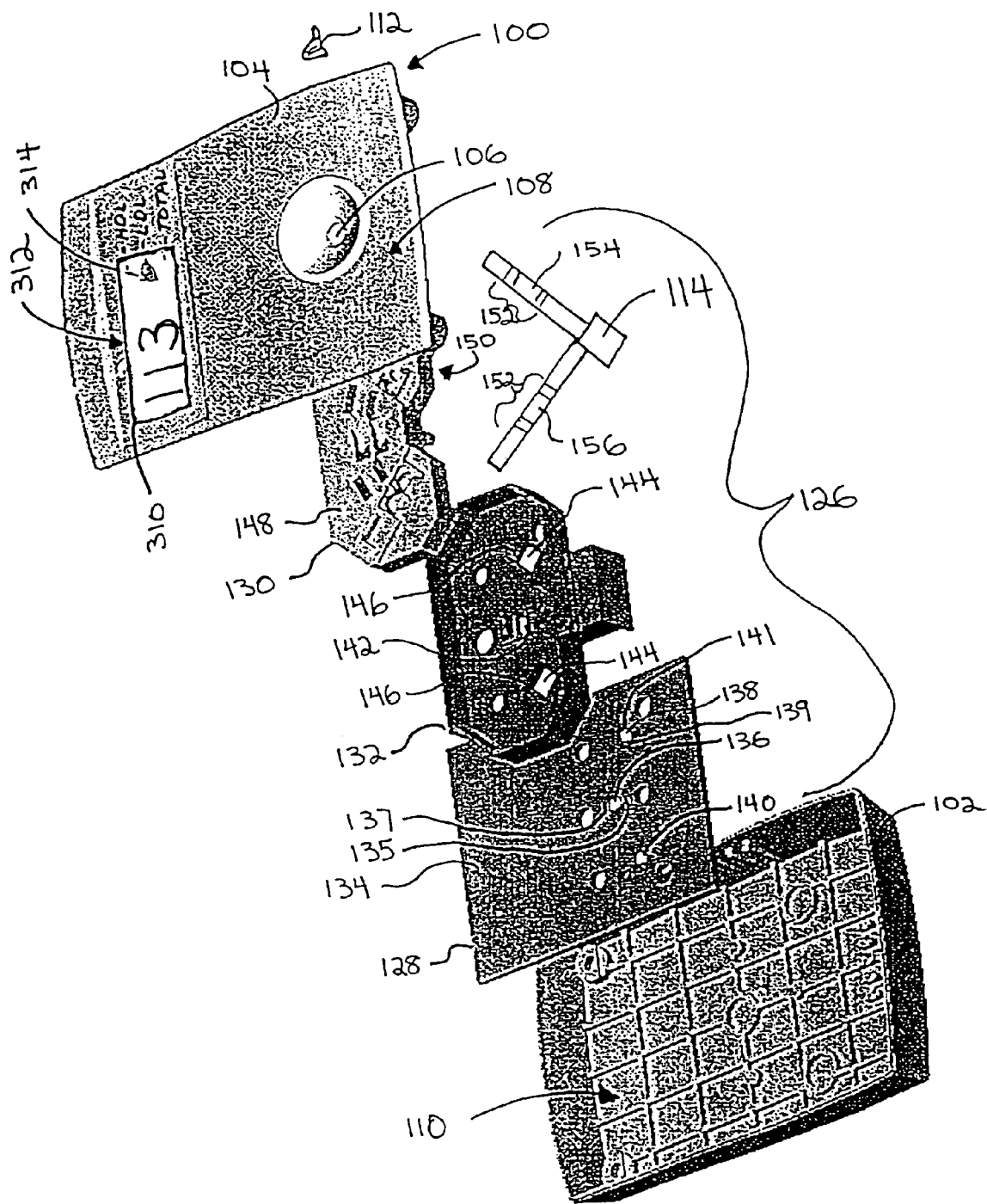
FIG. 1 is an exploded perspective view of a preferred embodiment of a diagnostic device of the present invention.

The present invention is preferably utilized in the disposable single-use digital electronic instrument and assay devices described in detail in the above-identified patent applications previously incorporated by reference. The present invention is also usable with qualitative and non-instrumented diagnostic devices. A sample of bodily fluid is applied directly to any type of diagnostic device which relies upon the removal of one or more substances from the sample which may interfere with an accurate analysis of the sample.

Generally, the present invention directs a sample introduced to a diagnostic assay device to multiple detection areas. The sample flows in two dimensions laterally across a transport matrix and, subsequently, transverse to the transport matrix in a third dimension. The detection areas are separate and isolated from one another. There is no sample, or sample component, that is allowed to flow from one detection area to any other.

The present invention provides a metering layer which is located between the transport layer and each detection area. The metering layer inversely spreads the sample flow uniformly across the transport matrix. The metering layer then presents the sample flow to the detection areas at approximately the same time, regardless of their position along the transport matrix. More specifically, the present invention describes a general chemistry assay for use in a single-use diagnostic test device with a digital output. The assay uses dry reagent chemistry to quantitatively determine the rate of bone resorption. A urinary biochemical marker of bone resorption, N-telopeditide (NTx), is measured using a lateral flow immunoassay chemistry and enzymatic/colorometric chemistry measures creatinine. Using microelectronics, a diagnostic device delivers in a few minutes a digital output display of the assay results which are significantly more accurate than the prior art. Furthermore, the diagnostic device can be used with a sample which is unmeasured and undiluted or otherwise untreated prior to the samples application in the device. As a result, the diagnostic device can be used in point-of-care settings such as the home and even clinics and other professional offices that have limited access to a analytic results on a timely basis.

Substantially all types of assays can be carried out with the present invention for a wide variety of analytes. Assays that can be performed include, but are not limited to, general chemistry assays and immunoassays. Both endpoint and reaction rate type assays can be accomplished with the present invention.

Analyte, as used herein, is the substance to be detected which may be present in the test sample. For example, general chemistry assays can be performed for analytes such as, but not limited to, glucose, cholesterol, HDL cholesterol, LDL cholesterol, triglycerides, and BUN. For immunoassays, the analyte can be any substance for which there exists a naturally occurring specific binding member (such as, an antibody), or for which a specific binding member can be prepared. Thus, an analyte is a substance that can bind to one or more specific binding members in an assay. Analyte also includes any antigenic substances, haptens, antibodies, macromolecules, and combinations thereof. As a member of a specific binding pair, the analyte can be detected by means of naturally occurring specific binding partners (pairs) such as the use of intrinsic factor protein as a member of a specific binding pair for the determination of Vitamin B12, or the use of lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. In particular, such analytes include, but are not intended to be limited to, ferritin; creatinine kinase MB (CK-MB); digoxin; phenyloin; phenobarbital; carbamazepine; vancomycin; gentamicin, theophylline; valproic acid; quinidine; luteinizing hormone (LH); follicle stimulating hormone (FSH); estradiol, progesterone; IgE antibodies; vitamin B2 micro-globulin; glycated hemoglobin (Gly Hb); cortisol; digitoxin; N-acetylprocainamide (NAPA); procainamide; antibodies to rubella, such as rubella-IgG and rubella-IgM; antibodies to toxoplasma, such as toxoplasmosis IgG (Toxo-IgG) and toxoplasmosis IgM (Toxo-IgM); testosterone; salicylates; acetaminophen; hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B antigen (HBAg); antibodies to hepatitis B antigen (Anti-HB); thyroid stimulating hormone (TSH); thyroxine (T4); total triiodothyronine (Total T3); free triiodothyronine (Free T3); carcinoembryonic antigen (CEA); and alpha fetal protein (AFP). Drugs of abuse and controlled substances include, but are not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methaqualone; opiates such as heroin, morphine, codeine, hydromorphone, hydrocodone, methadone, oxycodone, oxymorphone, and opium; phencyclidine; and propoxyphene. The details for the preparation of such antibodies and their suitability for use as specific binding members are well known to those skilled in the art.

The sample to be tested by the present invention for the presence of an analyte can be derived from any biological source, such as a physiological fluid, including whole blood or whole blood components including red blood cells, white blood cells, platelets, serum and plasma; ascites; urine; sweat; milk; synovial fluid; peritoneal fluid; amniotic fluid; cerebrospinal fluid; and other constituents of the body which may contain the analyte of interest. The test sample can be pretreated prior to use, such as preparing plasma from blood, diluting viscous fluids, or the like; methods of treatment can involve filtration, distillation, concentration, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte. The analyte can be any compound or composition to be detected or measured and which has at least one epitope or binding site.

Single or multiple assays can be done at one time. For example, a single assay can be performed measuring cholesterol or one device can be set up to measure both total and HDL cholesterol from a single sample. One test device can be set up to measure one, two, three, or more analytes at one time.

The present invention can be used in assay devices having many configurations, some of which are specifically illustrated herein. Often these assay devices use a wicking member or transport matrix which is a porous material. By "porous" is meant that the material is one through which the test sample can easily pass and includes both bibulous and non-bibulous solid phase materials. In the present invention, the porous member can include a fiberglass, cellulose, or nylon pad for use in a pour and flow-through assay device having multiple layers for multiple assay reagents; a test strip for wicking or thin layer chromatographic capillary action (e.g., nitrocellulose) techniques; or other porous or open pore materials well known to those skilled in the art (e.g., polyethylene sheet material).

The assay devices include a sample receptor means for receiving a sample of bodily fluid, such as whole blood, containing at least one of a plurality of analytes selected for determining its presence. The sample receptor means is located on the exterior surface of the device housing and allows the sample to be applied to a sample pad, wicking material, transport matrix or the like. Subsequently, the interfering substances are removed from the sample to form a "clean" sample. The clean sample is in fluid communication with a sample treatment means for chemically reacting the clean sample with at least one chemical reagent corresponding to an assay. Each reagent chemically reacts with the clean sample in a corresponding reaction zone located on the transport matrix to produce a reaction product mixture corresponding to each reagent. The sample treatment means also transports at least a portion of each reaction product mixture to a corresponding detection zone located on the transport matrix. The sample treatment means is located within the housing and is in fluid communication with the sample receptor means. Alternately, the clean sample can react with the chemical reagent in the detection zone.

For immunoassays, the present invention preferably uses particle detection for a detectable response or signal in each reaction zone related to the level of analyte in the sample. Other means for providing a detectable response in the reaction zones are suitable for use in the present invention. For example, and not for limitation, the analyte may be labeled with an indicator to measure fluorescence or luminescence, or the reflectance or absorption of a characteristic light wavelength. As use herein, "indicator" is meant to include all compounds capable of labeling the analyte or conjugate thereof and generating a detectable response or signal indicative of the level of analyte in the sample.

Although the chemistry and configurations of the present invention may be used in an integrated assay device, the present invention can be used in any other instrumented reflectance or transmission meter as a replaceable reagent. Thus, the present invention also encompasses integrated assay instruments and analytical assay instruments comprising the present assay device.

A preferred embodiment of a single-use diagnostic device 100 is illustrated in FIG. 1. The device 100 includes a housing 102 and cover 104 having a receptor such as inlet port 106 which extends from the exterior surface 108 of the cover to the interior 110 of the housing for receiving a sample 112 containing the one or more selected analytes to be determined.

The inlet port 106 allows the sample 112 to be introduced to a sample receiving device 114 which is attached to the interior surface 116 of the cover 104. The sample receiving device 114 includes a pad which is in fluid communication with two assay strips and serves to distribute the sample between the two strips. Optionally, the sample receiving device 114 can also include a sample filter pad which removes undesired contaminants from the sample. The sample filter pad can be the same as the receiving pad with one pad performing bother functions. The device 100 can include more than one sample filter pad along the pathway of the sample flow which remove different types of contaminants. The two assay strips contain chemical reagents for determining the presence of one or more selected analytes.

The interior 110 of the housing encloses a reflectometer 126 which includes a printed wiring assembly having a printed circuit board (PCB) 128. The reflectometer 126 also includes an optics assembly 130 and a shield 132. The PCB 128 has one face 134 with a reference detector 136 and zone detectors 138, 140 mounted directly thereto. The face 134 of the PCB also has two LEDs 135, 137, one for each pair of illumination channels, mounted directly to the PCB. The LEDs 135, 137 are preferably in bare die form without an integral lens, enclosure, or housing. As a result, the LEDs 135, 137 provide illumination in all directions above the face 1.34 and are directed only by the optics assembly 130. Similarly, the zone detectors 138, 140 and reference detector 136 are bare die mounted directly to the face 134 of the PCB. The LEDs 135, 137 and the detectors 136, 138, 140 are all positioned in the same plane.

FIG. 1 also illustrates the position of the shield 132 relative to the PCB 128. Aperture 142 is provided through the shield 132 to prevent obstructing the LEDs 135, 137 and the reference detector 136. Openings 144 are provided to prevent obstructing zone detectors 138, 140. The shield 132 includes upstanding walls 146 which prevent stray radiation from entering the zone detectors 138, 140. The upstanding walls 146 are positioned adjacent the reflecting and refracting elements of the optics assembly 130 when the reflectometer 126 is fully assembled.

The optics assembly 130 is a generally planar support having at least a top face 148 and a bottom face 150. The bottom face 150 is configured to receive illumination from the LEDs 135, 137 and the optics assembly 130 directs the illumination to one or more sampling areas 152 on a first 154 and second 156 assay strip. The top face 148 of the optics assembly is also configured to transmit the diffusely reflected optical radiation returning from the sampling areas 152 to one or more of the zone detectors 138, 140.

One of the preferred embodiments of the present invention is a general chemistry assay for detecting the presence and amount of NTx. An unmeasured and previously untreated sample 112 of urine is applied to a sample pad where large particulate debris is removed and the pH and ionic composition are normalized. The sample then migrates by capillary action toward the interference removal zone. The sample then migrates laterally through a polyester transport layer, transversely through a metering membrane, and into the chemistry reagent membrane.

Figure 2:
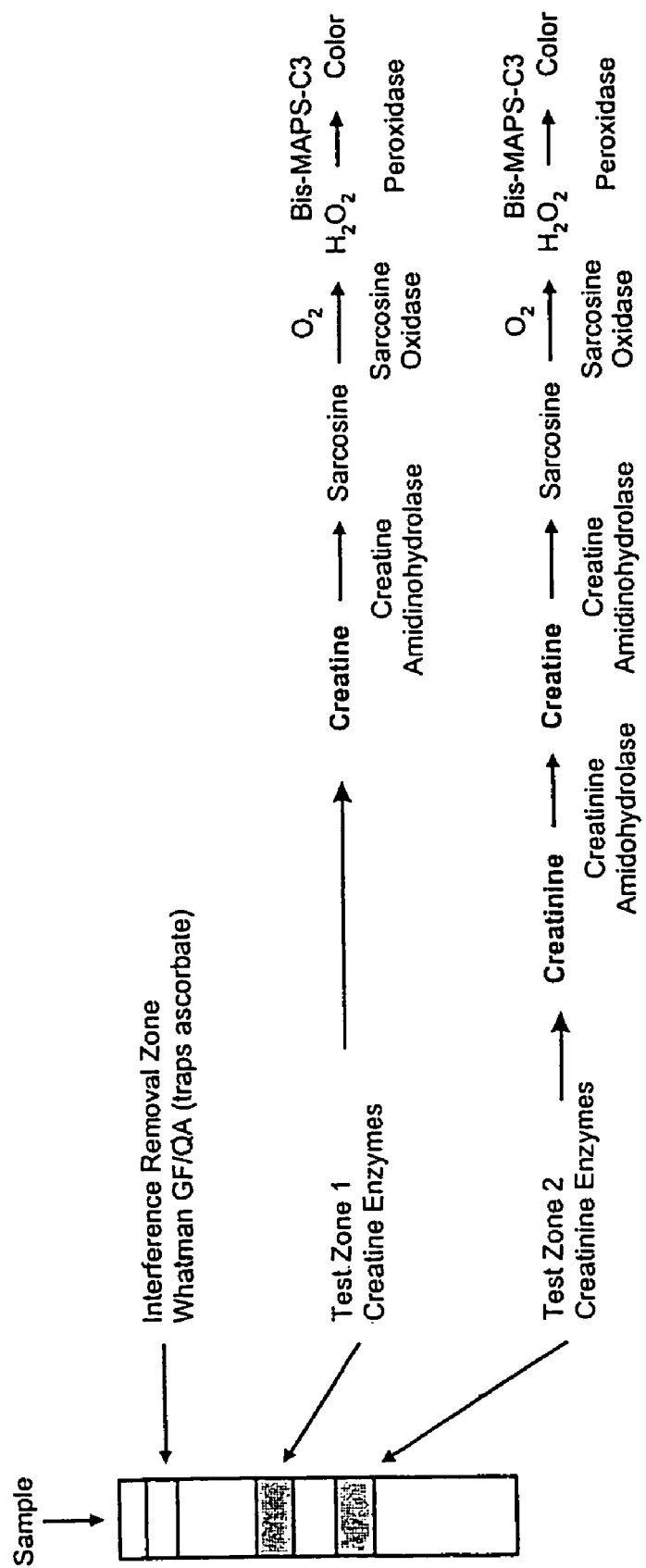
FIG. 2 is a top plan view of a creatinine dry reagent assay strip schematically illustrating the functional elements and chemical reactions involved in the assay.

The sample rehydrates the dry chemical reagents and the chemical reactions shown in FIG. 2 for a test zone 1 and a test zone 2 take place. The chemistry reagent layer for test zone 1 includes creatine amidinohydrolase, horseradish peroxidase (HRP), and indicators, along with appropriate surfactants, buffer components and co-factors. Test zone 2 further includes creatinine amidohydrolase. The Bis-MAPS-C3 is Bis(4-[N-3(3'-sulfo-n-propyl)-N-n-propyl]amino-2,6-dimethylphenyl) methane, disodium salt.

From the application of the sample to the completion of the reactions and generation of the color in test zones 1 and 2 is about a total of five minutes. The intensity of color generated on the chemistry strip in Test Zones 1 and 2 is proportional to the concentrations of creatine and creatinine+creatine total, respectively. The difference between the two test zones represents the net concentration of creatinine, alone.

Preferably, the test zones 1 and 2 are detection zones. When using the above described diagnostic device in FIG. 1, the reflectometer 126 detects the reflectance changes produced in test zones 1 and 2. Reflectance readings, $R_0$ and $R_1$ are made before and after application of the sample, respectively. Numerical concentration values are calculated based on calibration parameters determined in earlier experiments.

Figures 3A, 3B:
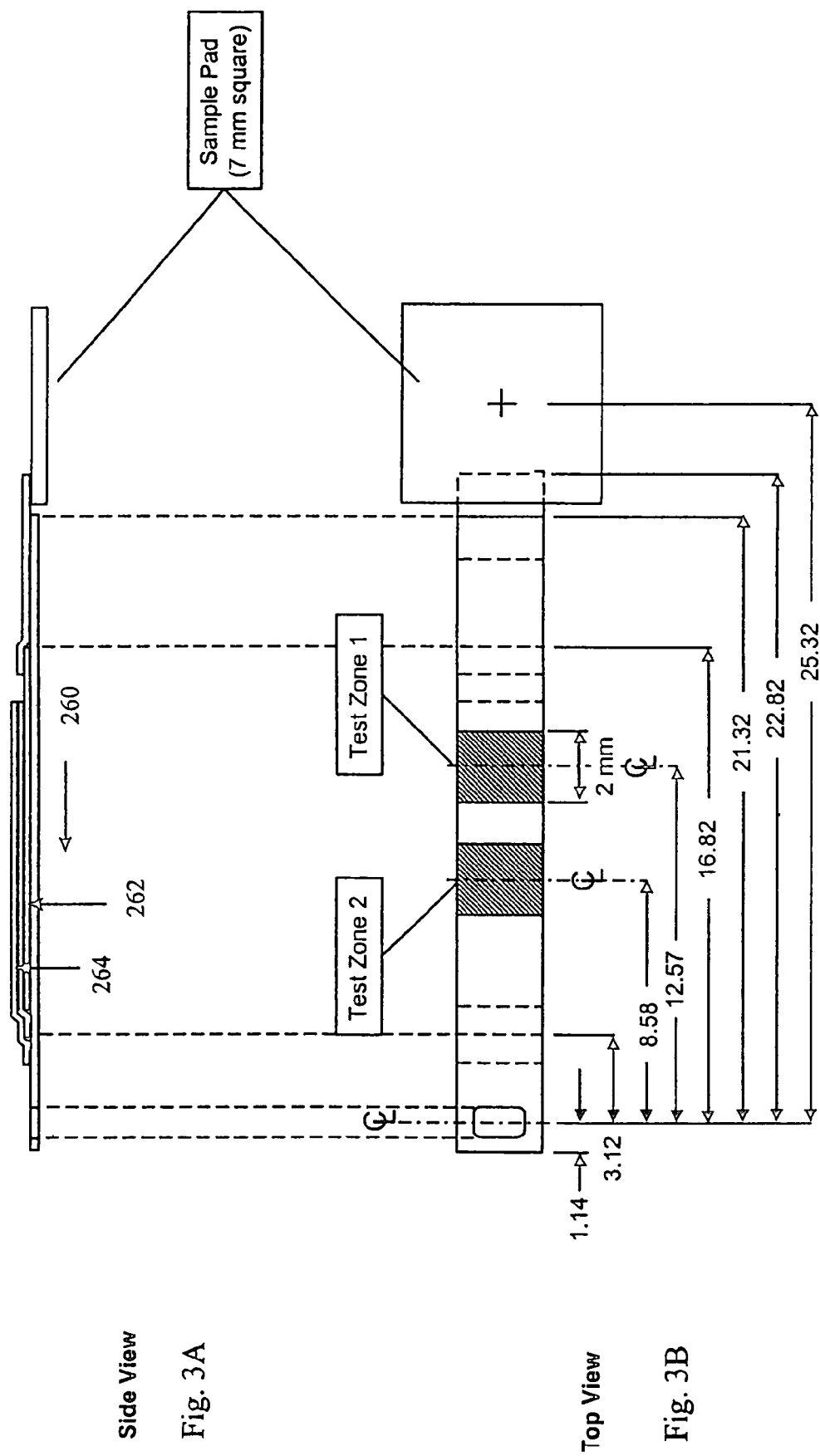
FIG. 3A is a side view of one embodiment of an assay strip suitable for use in a general chemistry assay.
FIG. 3B is a top view of one embodiment of an assay strip showing the layout from the membrane surface.

FIGS. 3A and 3B illustrate a laminated strip layout 230 for a creatinine or other general chemistry assay that is suitable for use in the preferred embodiment of the diagnostic device described above. Generally, there are four distinct pieces of porous material in fluid migration path of a strip 230, each of which are laminated to a backing 252 made of a suitable plastic like PET in precise alignment with each other. FIG. 3A shows a longitudinal cross-section along the fluid migration path while FIG. 3B shows the layout as viewed from the membrane surface. The sample wicks laterally as indicated by arrow 260 along a transport matrix 242. Then the sample wicks transversely as indicated by arrows 262 and 264 into test zones 1 and test zone 2, respectively. The strip 230 is held in alignment by a pin that fits into a sprocket hole 254 and by guides that fit against the side of the strip.

The strip layout 230 includes a sample pad 232 for receiving the sample through the inlet port (not shown) on the topside 234 of the pad 232 at the proximal end 236 of the strip 238. In the example of using the diagnostic device illustrated in FIG. 1, the sample pad, preferably not physically attached to the rest of the assay strip, receives the sample and divides it between a NTx strip and a creatinine strip.

The sample pad 232 is preferably made of CytoSep No. 1660 from Gelman Sciences which is a cellulose and glass fiber composite material. Another material which is suitable is GF/QA from Whatman. The GF/QA material from Whatman, Inc. of Fairfield, N.J. which is an quaternary ammonium cellulose matrix having a basis weight of about 68 $g/m^2$, a thickness of about 373 µm, and a mean pore size of 4.0 µm. The GF/QA material has a protein binding capacity for bovine serum albumin of 0.296 g/dg with a linear wicking (Klemm) of 2 min for a 7.5 cm rise and a derivative content of 2.0 $mg/cm^2$. The GF/QA material includes trimethylhydroxy propyl quaternary ammonium (QA) as a high performance strong base quaternary ammonium exchanger with fast kinetics, high protein capacity, and is effective over a wide pH range.

The sample pad material had approximately square dimensions of about 7 mm with a thickness of about 0.023 inches. The sample pad 232 attaches to and is in fluid communication with two assay strips like 114 and 116 previously illustrated in FIG. 1.

The sample flows from the sample pad 232 to a sample treatment pad 240 that is preferably made of the GF/QA paper from Whatman described immediately above. The sample treatment pad 240 is composed of a quaternary ammonium derived membrane for trapping ascorbate and other anionic interferents. The sample treatment pad 240 is attached by adhesive to a white PET backing. Another suitable material for the sample treatment pad 240 is Accuwik No. 14-20 from Pall Biosupport. The sample treatment pad 240 is preferably about 7 mm long and 3 mm wide with a thickness of about 0.00945 inches.

The sample treatment pad 240 overlaps and is in fluid communication with a transport matrix 242 preferably made of polyester substrate from Tetko P/N 7-2F777 BM having a size of about 11 mm long and about 3 mm wide with a thickness of about 0.00846 inches. The transport matrix 242 allows the treated sample to flow quickly towards the distal end 244 of the strip with a weave having a fast lateral wicking rate. The transport matrix 242 transports the sample into a metering or inverse spreading membrane layer 246 and a chemistry reagent membrane layer 248.

Substantially overlapping the transport matrix 242 is a metering or inverse spreading layer 246 that assists in spreading the treated sample across the length of the strip (transport matrix 242). The metering layer 246 serves to slow the migration of fluid into the reagent layer 248 until the transport matrix 242 is completely saturated. Preferably, the metering layer 246 is a Biodyne® Grade A 0.2 mm from Pall Biosupport which is composed of a nylon and has a uniform opacity that is retained after impregnation with indicator and enzyme mixtures and subsequent drying.

A reagent layer 248 substantially overlaps the metering (inverse spreading) layer 246 and contains the chemical reagents for performing the assay to produce a physically detectable change on the top surface 250 of the reagent layer that is measured by the detector previously described. The reagent layer 248 is effectively divided into two reaction zones—one measuring creatinine and the other measuring creatine. The true value for creatinine is obtained by subtracting the latter from the former. Preferably, the reagent layer 248 is Biodyne® Grade C, 5.0 mm from Pall Biosupport which is also a nylon and has a uniform opacity that is retained after impregnation with indicator and enzyme mixtures and subsequent drying.

The reagent layer 240 contains the dried chemical components needed to measure creatinine in the sample. An example of a suitable solution for dipping the indicator includes 0.5% w/v sucrose, 1.0% w/v polyvinyl-pyrrolidone (avg. mw. about 40,000), 5% v/v surfactant 10G(p-isononylphenoxy-poly(glycidol) and 75 mg/ml bis(4-(N-3'-sulfo-n-propyl)-N-n-propyl)amino-2,6-dimethyl-phenyl)methane, disodium salt; the enzyme solution used for dipping the reagent layer included 1000 u/ml horseradish peroxidase (EC 1.11.17), 0.500 u/ml sarcosive oxidase (EC 15.3.1), 500 u/ml creatinine amidinohydrolase (EC 3.5.3.3), 1200 u/ml creatinine amidohydrolase (EC 3.5.2.10) (all from the Toyobo Company), 1% w/v poly(vinyl alcohol)(avg. mw. about 70,000), 1% v/v Triton X-100 (t-octylphenoxypolyethoxyethanlo), 1% w/v sucrose, 5mg/ml Bovine Serum Albumin, and 50 mM buffer 3-(N-morpholino)-2-hydroxypropanesulfonic acid, sodium salt, pH 7.5.

Performance of each reagent or test strip configuration was evaluated using a final ratio reflectance reading, (R) wherein the final ratio value is calculated after the chemistry layer has reached its final color intensity. In order to compare various initial chemistry formulations and strip configurations, the equation of Kubelka and Munk was used to linearize the final R into K/S to convert reflectance into K/S so that $$K/S = \frac{(1-R)^2}{2R}.$$

Creatinine was then approximated to be a simple linear function of K/S. Later analyses utilized an empirical function that more closely yielded linear analyte to response so that, Creatinine=$A+B/R+C/R^2+D/R^3$. The equation was obtained using a computer program for least squares regression analysis called TableCurve from Jandel Scientific. The polynomial equation yielding the best fit, based on standard, error, was selected.

Having generally described the present invention, a further understanding can be obtained by reference to the following specific examples, which are provided herein for purposes of illustration only and are not intended to be limiting of the present invention.

EXAMPLE 1

Preparation of general chemistry strips for the detection of creatine and creatinine according to the present invention used three separate processes. The first process is to impregnate a roll of nylon membrane in a suspension of 15% Titanium Dioxide. This suspension is prepared by mixing in a high-speed mixer the follow components in successive order: 0.25g/mL 1% PVA 186K; 0.5966 g/mL distill Water; 0.00075 g/mL Tripolyphospate; 0.00075 g/mL Fumed Silicon Dioxide; and 0.15 g/mL Titanium Dioxide. After coating, the membrane is dried at 37° C. for 10 minutes and allowed to equilibrate to room condition for at least 8hours prior to the second coating.

The second process is to stripe two separate enzyme solutions simultaneously using a platform striper with a metered pump such as those made by IVEK of North Springfield, Vt. Other applicators suitable for use with the present invention include, but are riot limited to, a fountain pen, a pad printer, pipette, air brush, metered dispensing pump and tip system, or the like. Other applicators which accurately measure the reagents onto appropriate zones of the predetermined distribution are also suitable. Enzyme solution 1 is striped 2.25 mm from one edge of the processed nylon material impregnated with titanium dioxide and indicator. Enzyme solution 2 is striped 5.25 mm from the same edge. Solution 1 includes: 4000 U/mL Creatine Amidohydrolase; 1000 U/mL Sarcosine Oxidase; 1000 U/mL Horse Radish Peroxidase; 22.92g/L TES pH 7.0; 10 g/L Sucrose; 10 g/L Triton X-100; 0.1 g/mL Xanthan Gum; and pH 7.0. Solution 2 includes: 1000 U/mL Creatinine Amidinohydrolase; 4000 U/mL Creatine Amidohydrolase; 1000 U/mL Sarcosine Oxidase; 1000 U/mL Horse Radish Peroxidase; 22.92g/L TES; 10 g/L Sucrose; 10 g/L Triton X-100; and 0.1 g/mL Xanthan Gum.

The final process is to stripe an indicator solution over the enzyme striped enzyme zones. This coating process is analogous to the one describe above. The indicator solution includes: 0.0620 g/mL Bis MAPS C3; 0.25 mL/mL Isopropyl Alcohol; 0.005 g/mL Sucrose;0.05 mL/mL Surfactantant 10G; 0.05 mL/mL 20% PVP 40K; and 0.65 mL/mL Milli-Q water.

The metering (inverse striping) membrane layer is prepared by impregnating a roll of nylon membrane 10.51 mm wide in a buffer solution consisting of 250 mM MOPSO pH 7.5; and 0.5%(W/V) PVA 186K. This impregnating process is analogous to the dip and dry process for both the titanium dioxide and indicator.

The creatinine strip is prepared according to FIGS. 3A and 3B. A polyester fabric (Tetko 7-2F777, 11.1×3 mm), the metering (inverse spreading) membrane layer (10.51×3 mm), and the enzyme membrane (12.69×3 mm) is attached to a white PET backing with adhesive (Arcare 8072, 22.46×3 mil) in the order of sequence illustrated. The last step is to attack a glass fiber with quaternary ammonium groups (Whatman GF/QA, 7.0×3 mm) so that there is a 1.5 mm at the front end of the PET backing.

Conditions yielding the best proportionality between 15 and 20 mM creatinine standards (in K/S) were selected as optimal. The assay was run by loading 60 mL of a known creatinine standard into a diagnostic device similar to that described in FIG. 1. The progress of the enzymatic reaction was monitored until an endpoint was obtained which was typically 3 to 5minutes after application of the sample. Typical reaction progress curves are shown below in FIG. 4 for creatinine. Each reaction progress graph consists of four curves, two for each strip (test zones 1 and 2). Final $R/R_0$ values for each test zone were obtained by picking the minimum value over the period examined.

Figure 4:
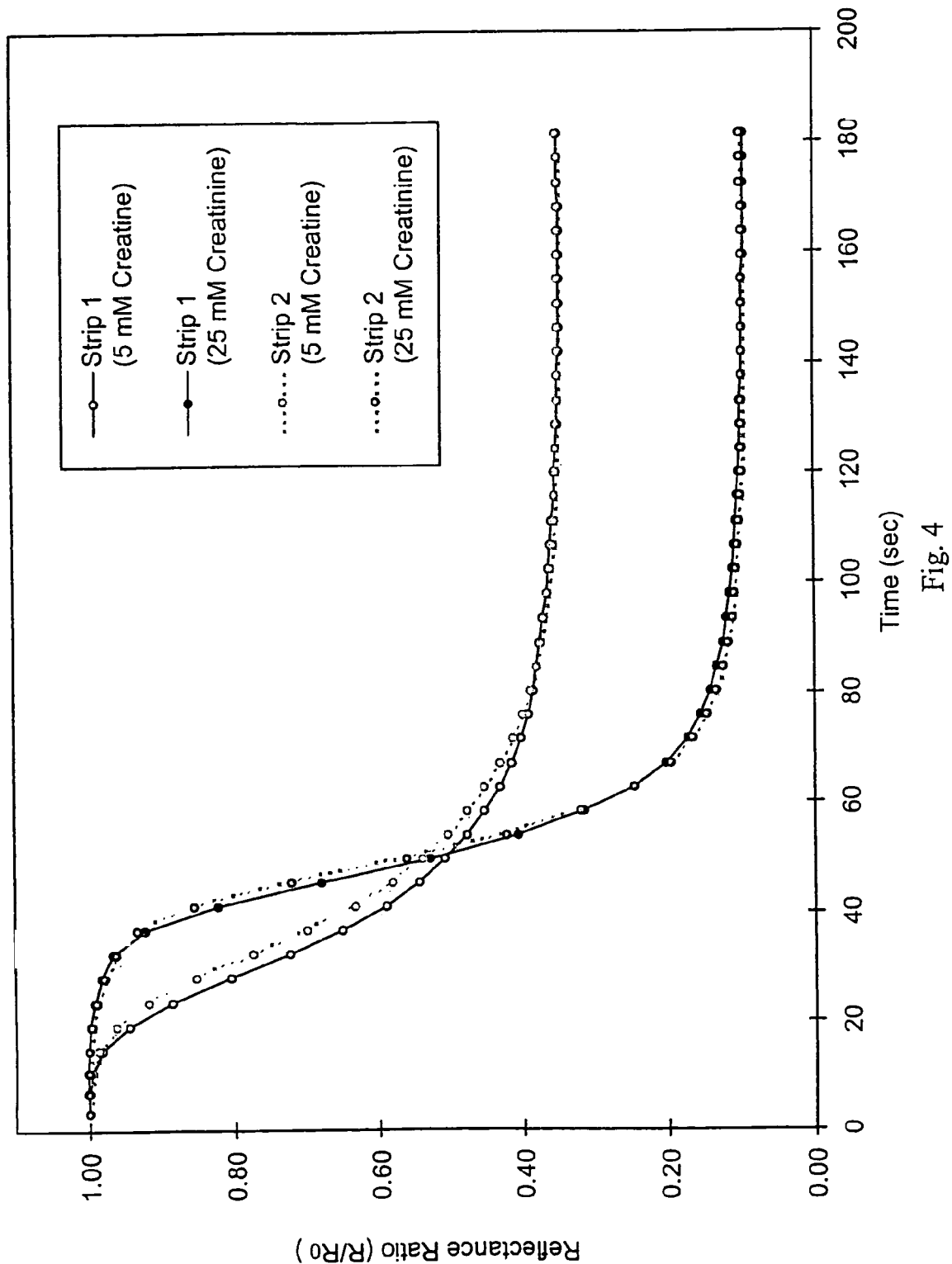
FIG. 4 is a graph showing the different responses of the two zones on each strip (Reflectance Ratio ($R/R_0$) verses the time in seconds)

The assay results depicted in FIG. 4 demonstrates the distinctly different response of the two zones on each strip, and the reproducibility between strips. Creatine is analyzed on Test Zone 1 and creatinine is analyzed on Test Zone 2 of each strip. Two identical strips were run at the same time in the same diagnostic device. The sample contained 25 mM creatinine and 5 mM creatine (in buffer).

Figure 5:
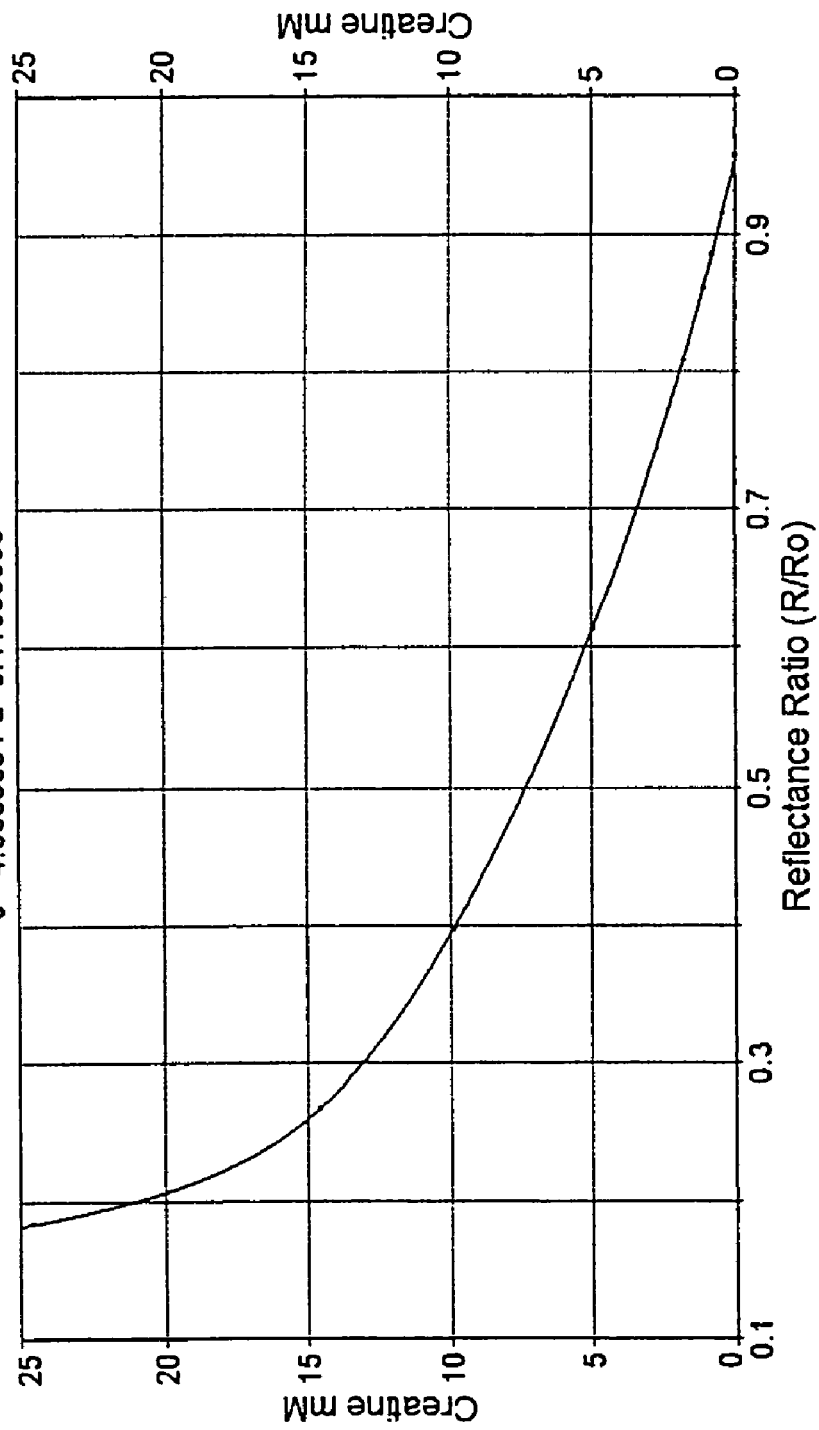
FIG. 5 is a graph showing the creatine calibration curve for zone 1 (creatine nM verses Reflectance Ratio ($R/R_0$)) wherein $y=a+b/x+c/x^2+d/x^3$ $r^2=1$ DF Adj $r^2=1$ FitStdErr=1.251856e-15 Fstat=1.2106292e+32 a=−13.836471 b=17.038182 c=−4.0603094 d=0.41099393.
Figure 6:
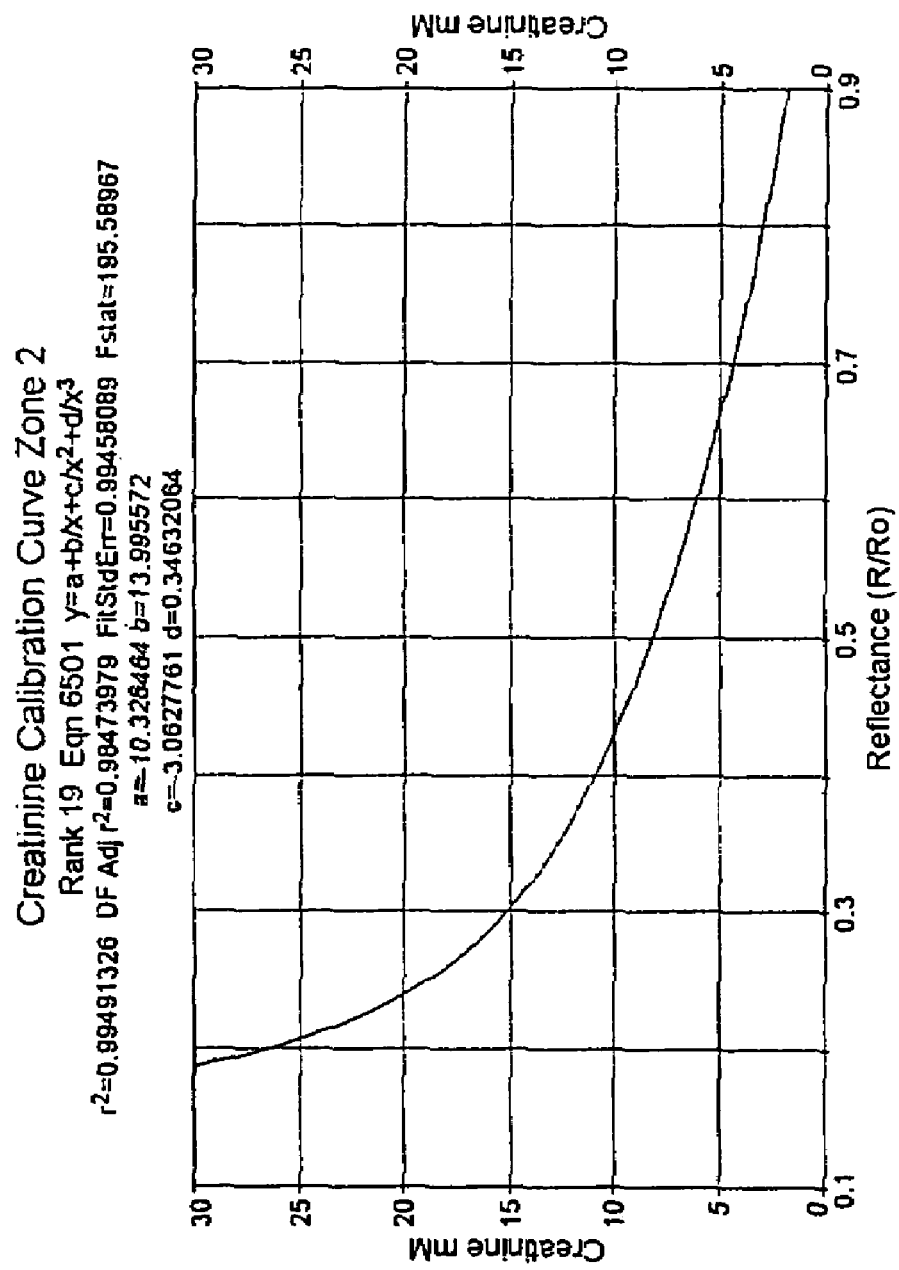
FIG. 6 is a graph showing the creatinine calibration curve for zone 2 (creatine mM verses Reflectance Ratio ($R/R_0$)) wherein $y=a+b/x+c/x^2+d/x^3$ $r^2=0.99491326$ DF Adj $r^1=0.98473979$ FitStdErr=0.99458089 Fstat=195.58967 a=−10.326464 b=13.995572 c=−3.0627761 d=0.34632064.

For determination of creatinine, the strips are placed in a GRETAG reflectance reader which can analyze disposable strips. A sample pad (Cytosep 1660, 7×7 mm) is placed over the end of the creatinine strip according to FIGS. 3A and 3B. A urine sample (100 μl) containing creatine or creatinine is added through the sample port of the reader that initiates reflectance readings to begin. The reader takes end point reflectance readings for both test zone 1 and test zone 2. A calibration curve generated for creatine (Zone 1) and creatinine (Zone 2) serves to determine the unknown concentrations of these analytes. FIGS. 5 and 6 show calibration curves for test zone 1 and test zone 2 respectively. To determine creatinine, the test zone 1 interpolated value is subtracted from the value of test zone 2.

Figure 7:
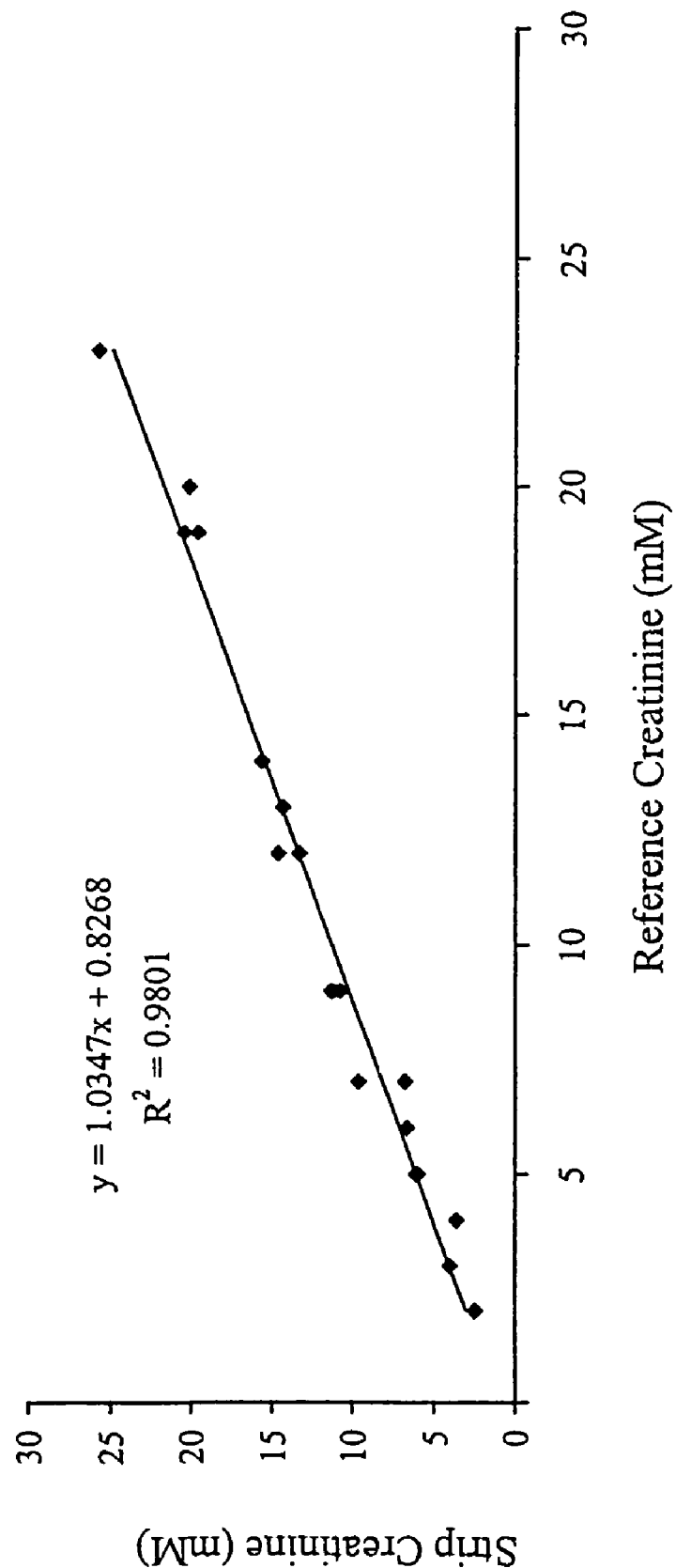
FIG. 7 is an accuracy graph for L/N 98-01-0033 (strip creatinine (mM) verses reference creatinine (mM) wherein y=1.0347x+0.8268 $R^2$=0.9801.

The clinical accuracy of the present invention was demonstrated using 20 urine samples was ran on creatinine strips according to the above procedure. Strip assigned values was than correlated to the reference value generated using a commercially available creatinine test kit. FIG. 7 shows the correlation graph.

The clinical precision of the present invention was demonstrated using three creatinine spiked urine samples. Each sample was repeated N=20. Reflectance values for creatinine was measured according to the above procedure. Precision results are summarized in Table I.

TABLE I

Precision Results

|  | 5 mM Precision | 10 mM Precision | 20 mM Precision |
| --- | --- | --- | --- |
| Mean | 4.84 | 10.90 | 21.31 |
| SD | 0.23 | 0.70 | 1.31 |
| % CV | 4.78 | 6.45 | 6.14 |

EXAMPLE 2

Figure 8:
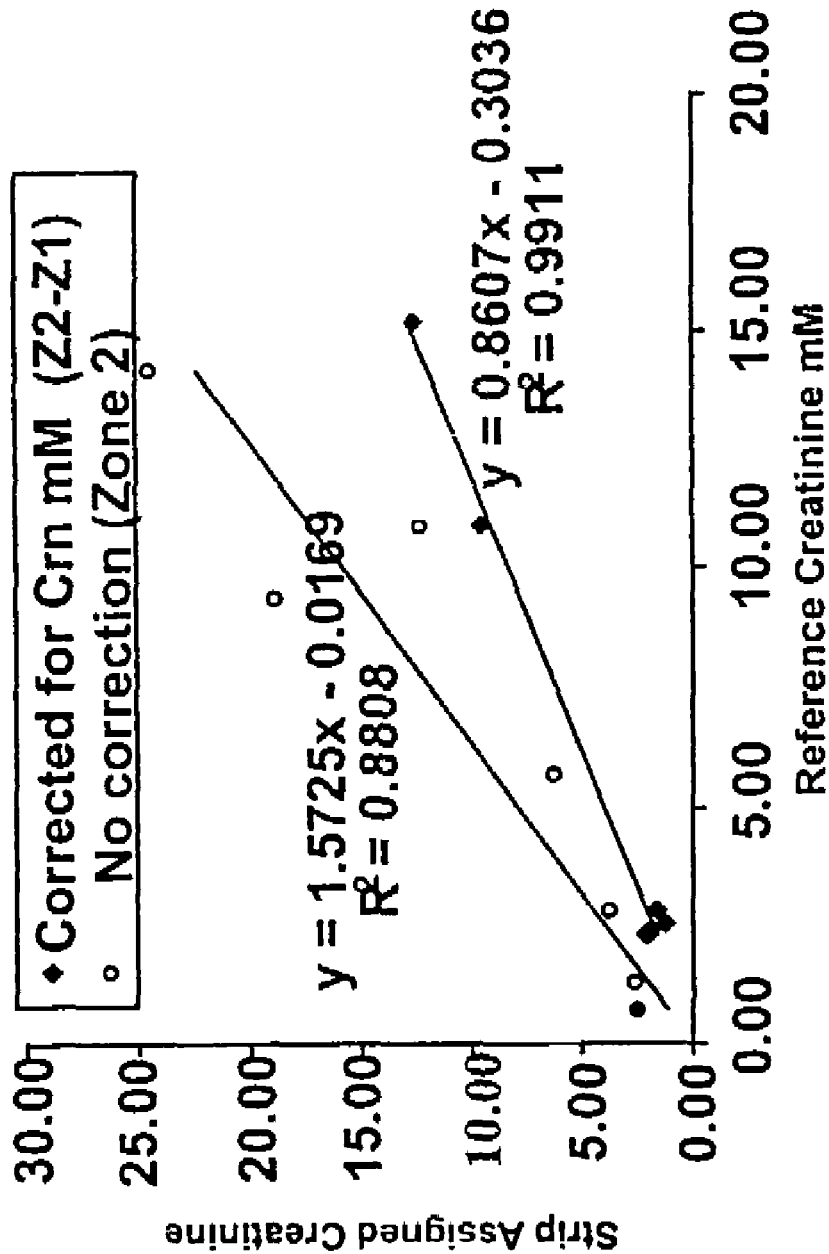
FIG. 8 is a graph showing creatine correction (strip assigned creatinine verses reference creatinine mM) wherein y=1.5725x−0.0169 $R^2$=0.8808 for no correction (zone 2) and wherein y=0.8607x−0.3036 $R^2$=0.9911 corrected for Cm mM (Z2−Z1)

In this example, the effectiveness of the creatinine strip of the present invention to correct for creatine in a sample is demonstrated. Urine samples were spiked with known amount of creatine and creatinine. The range for each did not exceed 15 mM for either analyte. A modified reference assay from Boehringer Mannhiem Corp. was used to find the reference value for both creatine and creatinine in these samples. Creatinine strips were run according to Example 1. Calibration curves for both test zone 1 and test zone 2 were performed according to Example 1. The measurement of test zone 1 represents the amount of creatine in a sample and the measurement of test zone 2 represents the sum of creatine and creatinine in a sample. To correct of creatine, the value of test zone 1 is subtracted from the value of test zone 2. The results from these samples are summarized in Table 2. FIG. 8 presents a graph showing the correlation between the reference assay and the strip assay with and without the creatine correction. FIG. 8 demonstrates that the strip assay of the present invention correlates very well with the reference assay when the value measured in test zone 1 is subtracted from the sum value measured in test zone 2. Without creatine correction, the measurement of the samples generally over-quantitate and correlate poorly with the reference assay. FIG. 8 effectively compare the results of the present invention with the prior art and demonstrates a significant improvement.

TABLE 2

Creatine Correlation

| Sample | Reference Creatine mM | Reference Creatinine mM | (Zone 2) Sum of Crt + Crn (mM) | (Zone 1) Crt mM | Corrected for Crn mM (Z2 − Z1) |
| --- | --- | --- | --- | --- | --- |
| 1 | 0.70 | 2.30 | 2.46 | 0.29 | 2.17 |
| 2 | 1.30 | 2.30 | 2.62 | 0.66 | 1.96 |
| 3 | 2.80 | 2.40 | 3.81 | 1.92 | 1.89 |
| 4 | 5.70 | 2.50 | 6.25 | 4.94 | 1.31 |
| 5 | 10.90 | 2.80 | 12.27 | 10.69 | 1.58 |
| 6 | 9.40 | 10.90 | 18.79 | 9.30 | 9.49 |
| 7 | 14.20 | 15.20 | 24.46 | 11.92 | 12.54 |

EXAMPLE 3

Figure 9:
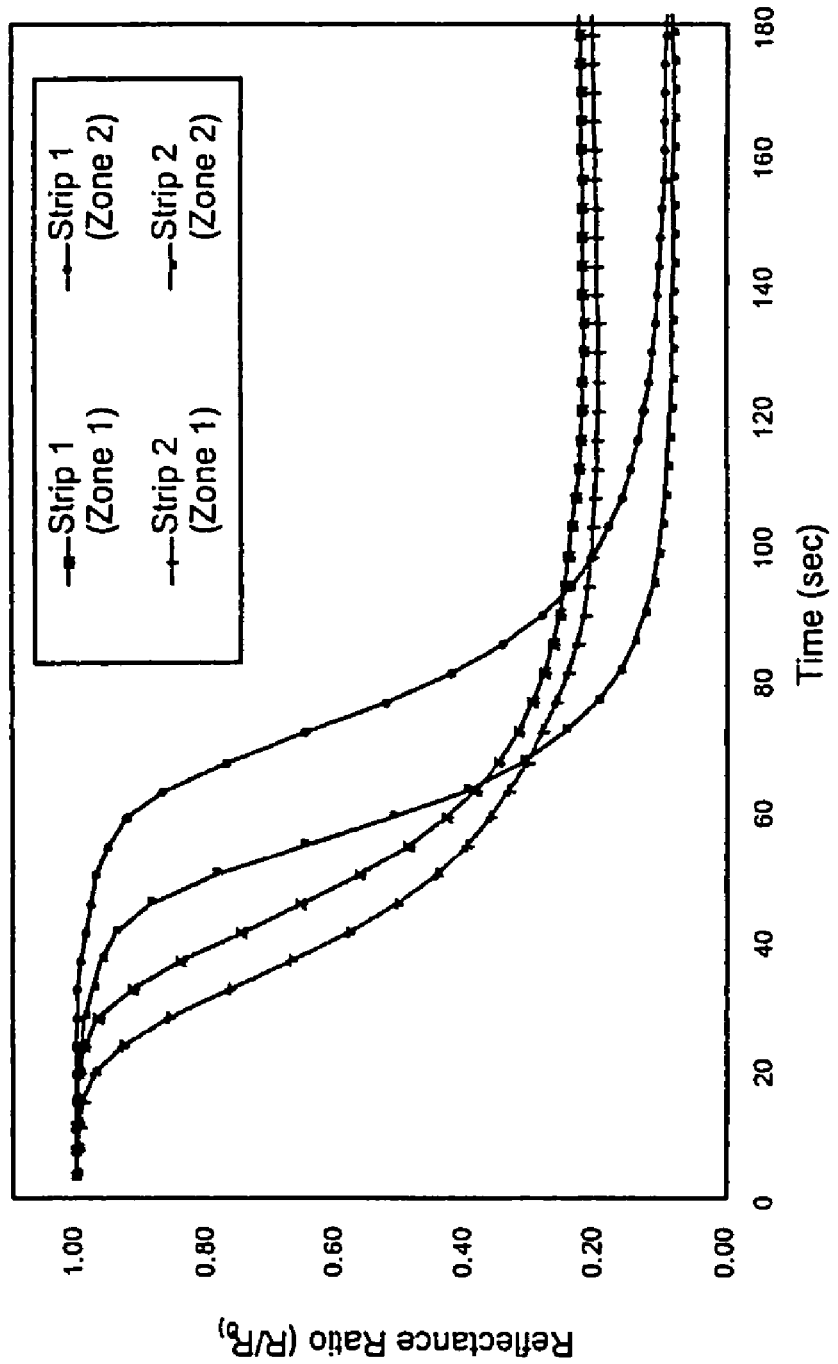
FIG. 9 is a graph showing strip performance without a hydrophobic barrier between Zone 1 and Zone 2 (Reflectance Ratio ($R/R_0$) verses the time in seconds)
Figure 10:
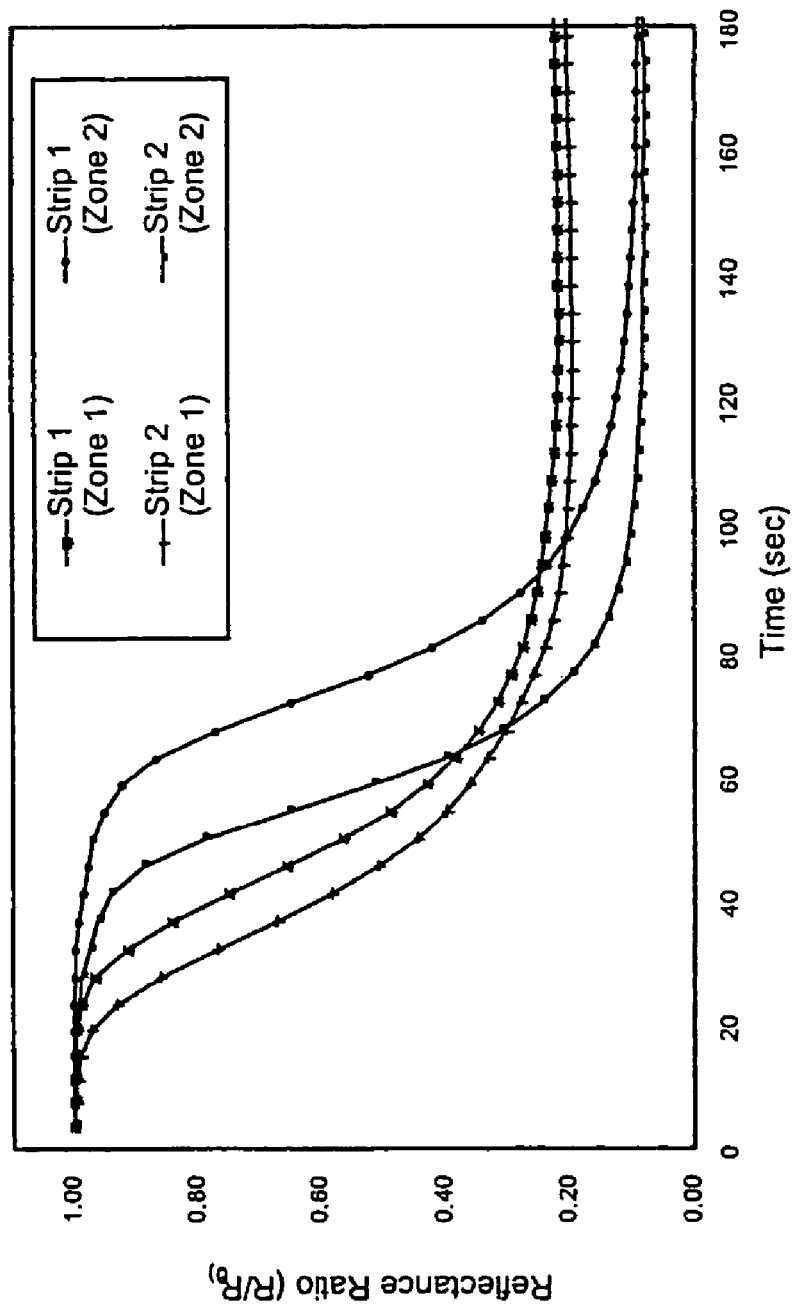
FIG. 10 is a graph showing strip performance with a hydrophobic barrier between Zone 1and Zone 2 (Reflectance Ratio ($R/R_0$) verses the time in seconds)

In this example, performance of an assay strip of the present invention with and without a hydrophobic barrier between Zone 1 and Zone 2 is compared. Creatinine enzyme membranes were prepared according to Example 1. In one set of chemistry reagent membranes, a 0.5 mm wide hydrophobic solution was striped. A second set of chemistry reagent membranes was prepared without a hydrophobic barrier. A sample spiked with 10 mM creatine and 20 mM creatinine was used according to Example 1. Kinetic profiles of the reflectance ratio (R/Ro) over time are illustrated in FIGS. 9 and 10 for assay strips without and with the hydrophobic zone, respectively. The profiles illustrated in FIGS. 9 and 10 showed little difference observed by adding the hydrophobic zone. If a rapid increase in R/Ro in test zone 1 had been observed after the strips began developing, diffusion of the sample from test zone 1 into test zone 2 would have been indicated. Based on these profiles, no detectable diffusion of the sample from test zone 1 into test zone 2 was observed. Lack of diffusion from one test to the other further indicates simultaneous delivery of the sample to each test zone regardless of position along the lateral flow of the sample in the transport matrix.

EXAMPLE 4

Figure 11:
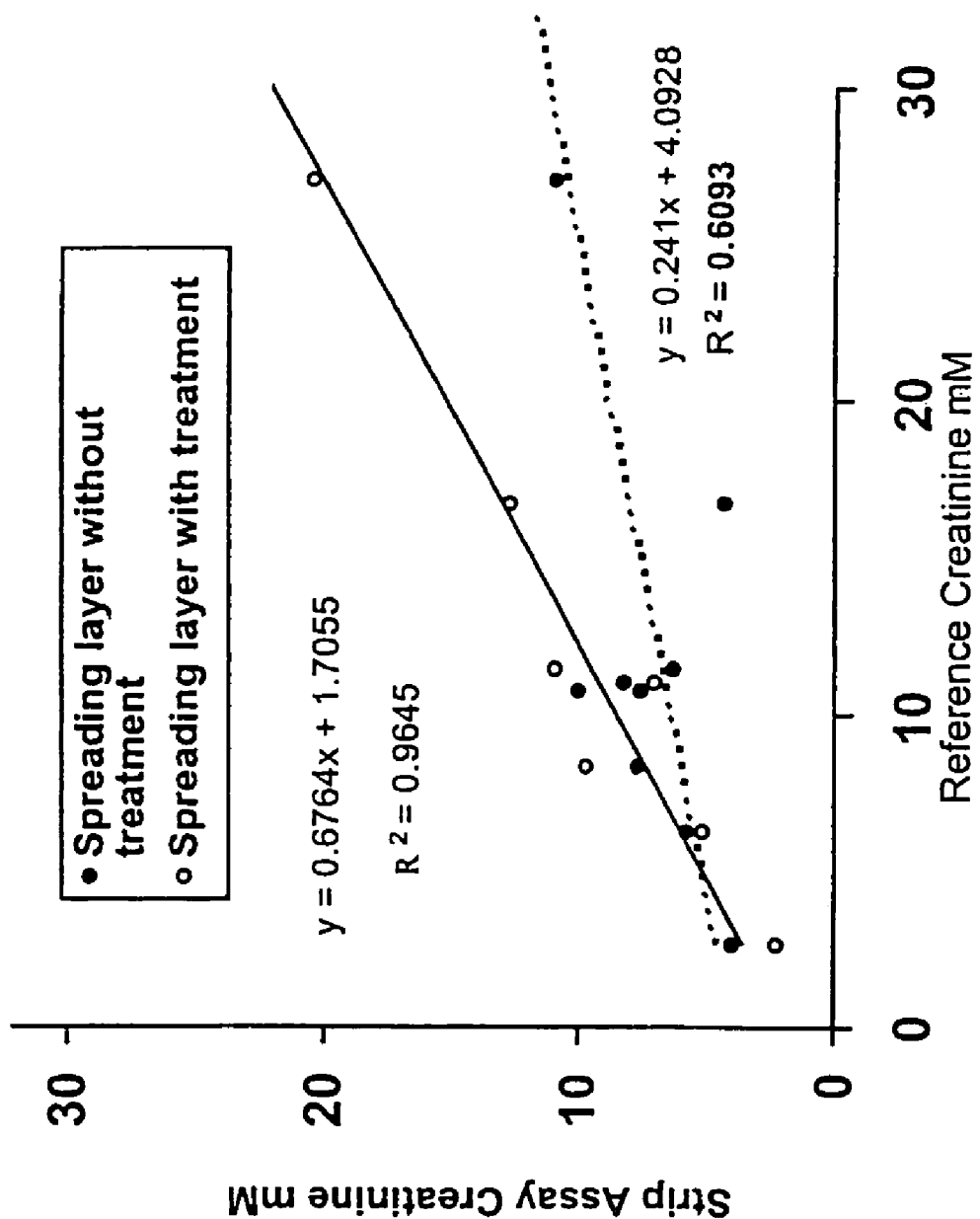
FIG. 11 is a graph showing the effectiveness of the spreading layer to pretreat patient sample (strip assay creatinine mM verses reference creatinine mM wherein y=0.6764x+1.7055$R^2$=0.9645 for spreading layer with treatment and wherein y=0.241x+4.0928 $R^2$=0.6093 for spreading layer without treatment.

In this example, the effectiveness of the metering (inverse spreading) layer to pretreat a patient sample is demonstrated. Creatinine strips were assembled according to Example 1, except that one set of strips did not use the metering (inverse spreading) layer treatment to pretreat the sample with the MOPSO buffer solution. Two sets of eight urine samples were evaluated for creatinine, according to Example 1. One set used the MOPSO buffer solution as a sample pretreatment in the metering (inverse spreading) layer. The other set used no sample pretreatment. A correlation plot against the reference value for these samples is illustrated in FIG. 11 and shows poor correlation for samples that were ran on strips without sample pretreatment.

The present invention also provides a lateral flow immunoassay strip for use in an instrument system that can produce qualitative or quantitative results. A preferred embodiment of the present invention provides an assay strip including three zones of which two zones are test zones and one of the test zones is a reference zone. A first test zone produces a signal with intensity inversely proportional to analyte concentration and a second test zone acts as a reference and produces a signal that is directly proportional to analyte concentration. The sum of the signals from test zones 1 and 2 is substantially equal at all analyte concentrations. Quantitative or qualitative results are achieved by instrumental reading of color intensity on test zone 1, test zone 2 or both test zones 1 and 2. The results expressed by any one test zone can also be determined as a proportion of the sum of the actual results expressed by both test zones. Quality reference is achieved by instrumental reading of both test zones, the sum of which should be substantially constant within a specified range.

The present invention provides an assay method having an inhibition type configuration. Again referring to FIG. 12, at the proximal end 11 of the strip 12 is the first zone 14 which includes a bibulous material containing a diffusively immobilized, particle-linked antibody capable of binding sample antigen. The second zone 16 is separate and distinct from the first zone 14, and is located some distance toward the distal end 13 of the bibulous strip. The second zone 16 includes a bibulous material containing a non-diffusively immobilized antigen capable of being bound by the particle-linked antibody. The bibulous material of the second zone 16 can be the same or different from the bibulous material of the first zone 14.

The third zone 18 is separated and distinct from the second zone 16, and is located some distance toward the distal end 13 of the bibulous strip. The third zone 18 includes a bibulous material which may be the same or different from the bibulous materials of the first and second zones 14 and 16 containing a non-diffusively immobilized first member of a specific binding pair capable of specifically binding to its specific binding partner which is the second member of the specific binding pair on the surface of the particle-linked antigen. This second member of the specific binding pair is not antigenically related to the sample antigen so it will not effectively compete with the antigen to bind to an anti-antigen monoclonal antibody.

The assay quantitation can be determined by reading the second zone 16, the third zone 18, or both second or third zones 16 and 18. The sample concentration output is a result of a calibration algorithm related to the second zone 16 alone, the third zone 18 alone or both second and third zones 16 and 18. This can result in a more reliable quantitative analyte concentration result. The summation of the detectable responses or signal from second and third zones 16 and 18 to produce a substantially constant total signal regardless of analyte concentration provides a reference mechanism for accurate assay performance.

The present invention provides a device which can be used to determine the presence of multiple analytes in a test sample. One test zone corresponds to each analyte selected for determining its presence. Each test zone receives and contacts the sample and a labeled indicator reagent corresponding to the selected analyte with a test zone reagent corresponding to the selected analyte. The test zone reagent corresponds to the selected analyte reacting in the presence of the sample and the labeled indicator reagent corresponding to the selected analyte to form a corresponding test zone reaction product and a corresponding test zone detectable response inversely related to the selected analyte level in the sample.

One reference zone receives the labeled indicator reagent not reacted with its corresponding test zone reagent from all the test zones. The reference zone contacts each labeled indicator reagent with a corresponding reference zone reagent. Each reference zone reagent reacts in the presence of the corresponding labeled indicator reagent to form a corresponding reference zone reaction product and a corresponding reference zone detectable response related to each selected analyte level in the sample and proportionately related to the corresponding test zone detectable response to establish a substantially constant total detectable response for a pre-determined range of each selected analyte. The detectable responses from each test zone are separately combined with the detectable result from the reference zone to determine each selected analyte level in the sample.

Figure 12:
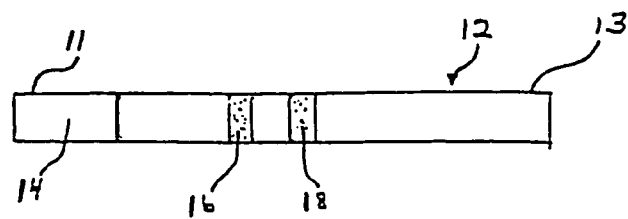
FIG. 12 shows a top surface view of an embodiment having typical structure with three reagent zones that can be used for quantitative and qualitative immunoassays.
Figure 13:
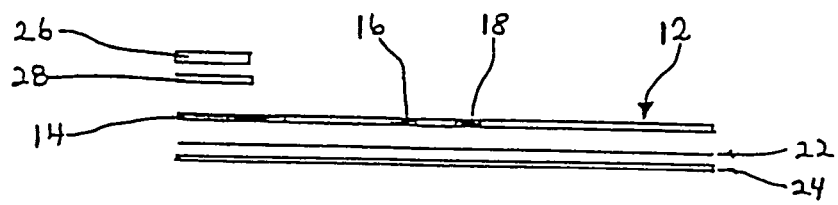
FIG. 13 shows an exploded lengthwise cross section of an embodiment having a typical structure with a sample pretreatment/filtration/separation/blood separation device.

FIG. 13 shows an exploded lengthwise cross section of the embodiment of FIG. 12 with one type of sample pre-treatment. The sample pre-treatment can include any combination of chemical, filtration or separation treatments, including blood separation. The sample treatment zone may be composed of one, two, or several layers of depth filter material 26 (such as glass fiber, metal fiber, synthetic fiber, paper, or natural or synthetic fabric) and a membrane 28 (such as S&S cellulose acetate, nitrocellulose, regenerated cellulose having an average pore size of from about 0.2 µm to about 7 µm, and Nucleopore or Poretics polycarbonate at pore sizes of about 0.2 µm to about 5 µm).

The layers of materials 26 and 28 can contain any number of assay reagents including but not limited to buffers, salts, proteins, enzymes and/or antibodies (either or both of which may be diffusively or non-diffusively bound to a particle or the bibulous material), polymers, small molecules, or any combination thereof. If red blood cells are to be separated, then layers of materials 26 and 28 function to remove substantially all of the red blood cells from the blood sample, leaving plasma to operate in the assay.

As shown in FIG. 13, sample filtration 26 and 28 is positioned immediately above and in fluid communication with the first zone 14. The sample filtration 26, 28 can be of any dimensions which effectively remove red blood cells from a whole blood sample to be assayed, and are preferably from about 0.2 to about 1 cm in length. The sample filtration can be secured with adhesive or be held in place by the instrument housing. The adhesive for affixing the sample filtration means in place may be any adhesive, such as epoxy, hot melt glue, or the like, or an adhesive tape such as that made by the 3M company.

Figure 14:
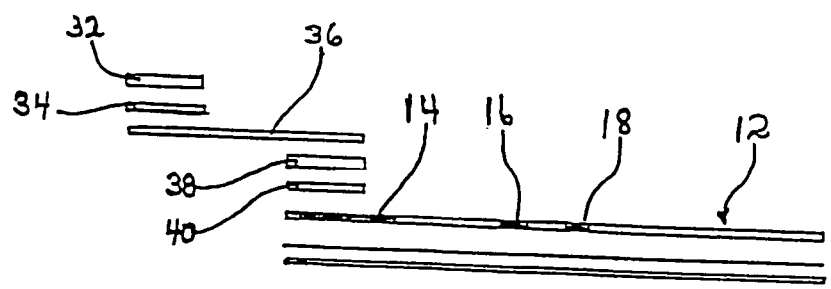
FIG. 14 shows an exploded lengthwise cross section of an embodiment having a typical structure with a sample pretreatment/filtration/separation/blood separation device and a sample transport.

FIG. 14 shows an exploded lengthwise cross section of the embodiment of FIG. 1 with a second type of sample pre-treatment and transport means. The sample treatment in the device of FIG. 14 can include any combination of chemical, filtration or separation means, including blood separation means. The sample treatment and transport device of FIG. 14 includes a sample application zone at filter 32, a membrane 34, a transport mesh 36, a second filter 38 add a membrane 40.

The filter 32 can be composed of one, two, three or more layers of any bibulous material, preferably a depth filter such as glass fiber, metal fiber, synthetic fiber, paper, or natural or synthetic fabric. Filter 34 can be one or several layers and is composed of any microporous membrane such as S&S cellulose acetate, nitrocellulose, regenerated cellulose at pore sizes from about 0.2 µm to about 7 µm, Nucleopore or Poretics polycarbonate at pore sizes of about 0.2 µm to about 7 µm.

Although filters 32 and 34 are shown in FIG. 14, one or both of these layers may not be necessary and can be excluded. In the case where both filter layers 32 an 34 are excluded, the sample will be applied directly to the transport layer 36.

The sample transport layer 36 is designed to accept the sample, either directly or through the filter layers 32 and 34, and move it horizontally to the area of filter 38. This sample movement may take from about 2 seconds to about 10 minutes, preferably from about 2 seconds to about 5 minutes, and more preferably from about 5 seconds to about 2 minutes.

The sample transport is composed of any bibulous material including, but not limited to, fabric or mesh that is woven or cast, synthetic or natural, and made of cotton, nylon, polyester, polypropylene, polyethylene or the like; paper such as Whatman 31ET or 3MM; glass fiber such as Whatman GFA, GFD, S&S 3362 or 32; plastic fiber, metal fiber and/or any synthetic membrane. The sample transport area can be untreated, or may have diffusively or non-diffusively immobilized therein one or more reagents such as stabilizing proteins, detergents, anticoagulants like heparin or EDTA, precipitating reagents, salts, proteins, enzymes, antibodies, enzyme-particle conjugates, antibody-particle conjugates, antigen-particle conjugates, red cell agglutinating agents like wheat germ lectin or anti-human RBC, polymers and/or small molecules.

The sample transport layer/zone 36 has dimensions sufficient to permit any desired sample pre-treatment without adversely affecting assay reactions and indicator measurements, but is preferably about 0.5 cm to about 5 cm (more preferably about 1 cm in length)in length and about 0.1 to about 1.5 cm (more preferably about 0.2 to about 0.5 cm) in width.

The filter 38 can be composed of one, two, three or more layers of any bibulous material, preferably a depth filter such as glass fiber, metal fiber, synthetic fiber, paper, or natural or synthetic fabric. Filter 40 can be one or several layers and is composed of any microporous membrane such as S&S cellulose acetate, nitrocellulose, regenerated cellulose at pore sizes from about 0.2 µm to about 7 µm, Nucleopore or Poretics polycarbonate at pore sizes of about 0.2 µm to about 5 µm. Although filters 38 and 40 are shown in FIG. 14, one or both of these layers may not be necessary and can be excluded. In the case where both filter layers 38 and 40 are excluded then the sample will be transported directly from the transport layer 36 to the first zone 14. All of the sample treatment and transport materials 32, 34, 36, 38, and 40 are in fluid communication with each other and with the first zone 14.

If the device is used for blood separation then it will function to remove substantially all of the red cells from the blood sample, leaving plasma to operate in the assay. The red cells can be substantially removed by filters 32 and 34 prior to the sample contacting the transport mesh or the red cells can be removed by filters 38 and 40 in which case the whole blood will travel on the transport layer. In a preferred embodiment, filters 32 and 34 are absent and sample blood or urine or any other body fluid is applied directly to the transport layer and sample treatment, filtration and/or blood separation occurs at filters 38 and 40.

Filters 32, 34, 38, and 40 have dimensions sufficient to permit any desired sample pre-treatment without adversely affecting assay reactions and indicator measurements, but preferably are about 0.2 cm to about 2 cm (more preferably about 0.25 to about 0.75 cm) in length and about 0.1 to about 1.5 cm (more preferably about 0.2 to about 0.5 cm) in width. The components of the sample treatment means and transport means of FIG. 5 can be secured with adhesive or held in place by a rigid housing. The adhesive can be any convenient adhesive including epoxy, hot melt glue, or the like, or may be an adhesive tape such as those made by 3M company.

Figure 15:
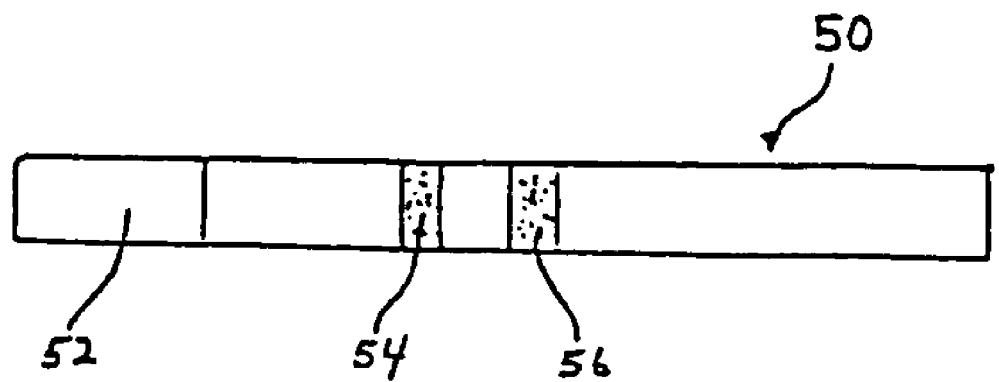
FIG. 15 shows the top surface view of one embodiment of the N-telopeptide (NTx) assay strip.
Figure 16:
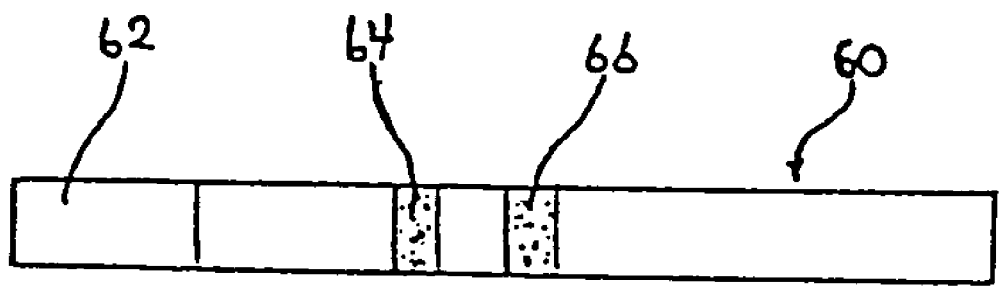
FIG. 16 shows the top surface view of a second embodiment of the N-telopeptide (NTx) assay strip.

Referring now to FIGS. 15 and 16, each of these immunoassay formats can have a sample treatment means and/or a transport means as described for the assay devices in FIGS. 4 and 14. Alternatively, they may have a sample treatment means as described for the assay device in FIG. 3.

FIGS. 15 and 16 show two embodiments of a quantitative assay to measure the concentration of the crosslinked bone collagen N-telopeptide (NTx) in urine, whole blood, plasma or serum. NTx is a product of bone resorption and is known to be present in urine and blood. The concentration of NTx is a direct measure of the rate of bone resorption and is a useful marker for (a) the onset of osteoporosis and (b) monitoring the progress of therapy for osteoporosis. Although NTx is shown as an example assay according to the present invention, it is understood that any analyte can be quantitatively or qualitatively measured.

The assay strips of FIGS. 15 and 16 each have two test zones. The two-test zone design provides improved performance in quantitative assays and improved reliability, since the sum of the signals from both test zones is substantially constant regardless of the analyte/antigen concentration, thus providing a robust quality reference and assuring accurate assay operation.

FIG. 15 is a top surface view of an inhibition type immunoassay configuration, a preferred embodiment of the present invention. In the assay strip 50, zone 52 contains a diffusively bound anti-NTx antibody (or any other antibody), conjugated to colloidal gold, colored latex beads or an enzyme. The diffusively immobilized anti-NTx-particle conjugate can also be located on filters 26 or 28 of the device of FIG. 13 or on filters 32, 34, 38 or 40 or transport layer 36 of the device of FIG. 14.

The antibody can be monoclonal (e.g., derived from fusion of spleen cells from an immunized mouse with a suitable immortal cell line in accordance with known methods; see *Kohlstein and Milner*, 1975) or polyclonal (e.g., prepared from any suitably immunized animal species in accordance with known methods).

A preferred embodiment uses conjugates of anti-NTx antibody to particles of colloidal gold, or to blue or black latex beads. Particles can be from about 5 nm to about 2000 nm in diameter (more preferably from about 5 nm to about 500 nm in diameter).

Diffusive immobilization can be conducted by formulating the assay reagent(s) to be immobilized (e.g., by dissolving in a suitable solvent such as water, a $C_1$-$C_4$ alcohol or mixture thereof, along with any desired additives), applying the resulting formulation to the bibulous material of the membrane, filter or transport layer in the desired location(s), and drying the material. Suitable additives may include detergents, proteins, blocking agents, polymers, sugars or the like. Alternatively, the additive(s) and assay reagent(s) may be applied to the membrane, filter or transport layer by precoating with a "blocking agent", water soluble polymer, sugar or detergent, followed by depositing the conjugate or conjugate formulation and drying the material.

Zone 54 is the first test zone of strip 50. Zone 54 contains non-diffusively bound NTx, NTx-macromolecule conjugate or NTx-particle conjugate. NTx is conjugated to a macromolecule or particle to help in the immobilization of the NTx peptide to the membrane (bibulous material) surface. Suitable macromolecules which can be used for NTx conjugation include any large molecule capable of adsorption or covalent binding to the membrane, including but not limited to: bovine serum albumin (BSA), keyhole limpet hemocyanin (KLH), immunoglobulin G (IgG), mouse IgG, bovine gamma globulin (BGG), lactalbumin, polylysine, polyglutamate, polyethylenimine, or aminodextran. Suitable particles which can be used for NTx conjugation can include particles of about 1-20 µm in diameter, including but not limited to, latex particles, microcapsules, liposomes or metal sol particles.

Non-diffusive immobilization can be accomplished by covalently attaching, adsorbing or absorbing the NTx, NTx-protein conjugate or NTx particle conjugate to the membrane. Suitable membranes for adsorption or absorption include, but are not limited to, S&S nitrocellulose and cellulose acetate at pore sizes from 0.45 µm to 12 µm, and Pall nylon at pore sizes of 0.45 µm to 20 µm (such as BIODYNE A, B, and C). Suitable membranes for covalent attachment include, but are not limited to, membranes such as Millipore IMMOBILON®, Gelman ULTRABIND® and Pall IMMUNODYNE® ABC. Alternatively, the antigen, antigen-protein conjugate or antigen-particle conjugate can be covalently attached to the membrane by chemically activating the membrane or paper prior to applying a solution or formulation of antigen/conjugate. Covalent attachment of the NTx peptide to the membrane occurs through a linkage to the primary amine on the NTx molecule.

Zone 56 is the second test zone of strip 50. Zone 56 contains a non-diffusively bound member of a specific binding pair capable of binding to a complementary member of the specific binding pair which is not related to the sample analyte/antigen on the surface of the particle-linked antibody.

For example, if the particle-linked antibody is a mouse monoclonal antibody, then the non-diffusively immobilized complementary binding partner in zone 56 can be any anti-mouse polyclonal or monoclonal antibody, including but not limited to: goat-anti-mouse, sheep-anti-mouse, cow anti-mouse, rabbit-anti-mouse, monoclonal rat anti-mouse or any other anti-mouse species antibody.

Alternatively, a generic binding partner such as Protein A, Protein G or Protein A/G (e.g., obtained from Pierce) can be non-diffusively immobilized at zone 56, as long as it binds the particle-antibody conjugate. Lectins can also be immobilized at zone 56, provided that the particle-antibody conjugate can be bound at this zone. Biotin, avidin or streptavidin can be linked to particle or to the particle-linked antibody, and the complementary binding partner may then be non-diffusively immobilized at zone 56.

For example, if biotin is conjugated to the particle along with the antibody, thus producing an anti-NTx-particle-biotin conjugate, then avidin or streptavidin can be non-diffusively immobilized at zone 56 and used to capture particles not bound in zone 54. Any non-human antigen, including proteins or small molecules such as dinitrophenol, known dinitrophenyl group-containing molecules or fluorescein can be co-conjugated with anti-NTx to the particle. The complementary antibody can then be immobilized to zone 56, the requirement being that the particle conjugate not bound in zone 54 is substantially all captured (bound) in zone 56 in the assay.

In the assay operation of FIG. 15, the sample is introduced to the proximal end of the assay strip in the area of the particle-linked antibody conjugate zone 52. The sample can be applied directly, or can be pre-treated, filtered, and/or separated as described above. The fluid sample (sample antigen, in this case NTx) then reconstitutes the particle-antibody (particle-anti-NTx) conjugate, and any antigen in the fluid sample is bound by the conjugate in zone 52. The particle-antibody conjugate is applied in excess, such that most of the antigen is bound by the conjugate.

The bound antigen:antibody-particle complex (NTx:anti-NTx-particle), as well as unbound antibody-particle (anti-NTx-particle) conjugate, migrate from zone 52 via capillary action to zone 54, where substantially all of the free antibody-particle conjugate is bound by the non-diffusively immobilized antigen (NTx) at this site. The antigen:antibody-particle complex cannot bind to the non-diffusively immobilized antigen at zone 54 since the binding sites are occupied by sample antigen. Consequently, the antigen:antibody-particle complex migrates via capillary action to zone 56 and is substantially all bound by the non-diffusively immobilized complementary member of the specific binding pair immobilized at this site.

At zero sample antigen concentration, the binding sites on the particle-antibody conjugate are free, and the particles are mostly bound at zone 54, where a dark color is produced. At very high sample antigen concentrations, the binding sites on the particle-linked antibody are mostly occupied, and the particles move past zone 54 and are substantially all bound at zone 56. Intermediate concentrations of sample antigen result in a predictable response relative to the bound particle signals at zones 54 and 56. In general, low sample concentrations result in high signal in zone 54 and low signal in zone 56. As analyte/antigen concentration increases, the signal in zone 54 becomes progressively lower, and the signal in zone 56 becomes correspondingly higher. The total signal, which is the sum of signal from zones 54 and 56, remains substantially constant across the entire concentration range. This provides a reliable quality reference for the assay result, since the sum of the signals must stay within a specified range. Otherwise, an assay failure is indicated.

Assay calibration and sample quantitative measurement can be achieved using zone 54 alone, zone 56 alone or both zones 54 and 56. Under certain conditions, one test zone may produce better performance in a particular analyte/antigen concentration range, and the other test zone may produce better performance in a different analyte/antigen concentration range. In this case, a hybrid calibration can be done that uses the optimal calibration range of each zone. Thus, the present two-test zone measurement provides substantial improvements over previously described methods.

FIG. 16 is a top surface view of a competitive-type immunoassay configuration, another preferred embodiment of the present invention. In the assay strip 60, zone 62 contains diffusively bound NTx (or other sample antigen) conjugated to colloidal gold, colored latex beads or an enzyme. The NTx can be coupled directly to the particle. Alternatively, NTx can be coupled indirectly to the particle through the macromolecule moiety of a macromolecule-NTx conjugate. The macromolecule used for NTx conjugation can be any large molecule capable of adsorption or covalent binding to the particle, including but not limited to: bovine serum albumin (BSA), keyhole limpet hemocyanin (KLH), immunoglobulin G (IgG), mouse IgG, bovine gamma globulin (BGG), lactalbumin, polylysine, polyglutamate, polyethylenimine, or aminodextran.

A preferred embodiment uses conjugates of NTx to particles of colloidal gold, or to blue or black latex beads. Particles can be from about 5 nm to about 2000 nm in diameter (more preferably from about 5 nm to about 500 nm in diameter).

The NTx-particle conjugate can also be diffusively immobilized on filters 26 or 28 of the device of FIG. 13 or on filters 32, 34, 38 or 40 or transport layer 36 of the device of FIG. 14. Diffusive immobilization can be accomplished as described above.

Zone 64 is the first test zone of strip 60. Zone 64 contains non-diffusively bound anti-NTx. Non-diffusive immobilization can be accomplished by covalent attachment or adsorption of the anti-NTx to the membrane as described above. Alternatively, anti-NTx can be conjugated to another protein, and this conjugate is then adsorbed to the membrane. Adsorption can be accomplished using membranes including, but not limited to, S&S nitrocellulose and cellulose acetate at pore sizes from 0.45 µm to 12 µm, and Pall nylon at pore sizes of 0.45µm to 20 µm (such as BIODYNE A, B, and C). Covalent attachment can be accomplished using membranes such as Millipore IMMOBILON®, Gelman ULTRABIND® or Pall IMMUNODYNE® ABC, or by chemically activating the membrane or paper prior to contacting the antibody with the membrane or paper.

Zone 66 is the second test zone of strip 60. Zone 66 contains a non-diffusively bound member of a specific binding pair such as an antibody or an antigen which is not immunologically related to the sample analyte/antigen, avidin, biotin, Protein A or G, lectin or the like) which binds to a complementary member of the specific binding pair on the surface of the particle-linked antigen. For example, if the particle is linked to both antigen and protein (e.g., an antigen-macromolecule-particle conjugate), then an antibody to that protein can be non-diffusively immobilized in zone 66.

Furthermore, for example, if NTx is conjugated to mouse IgG, and the particle is linked to this conjugate (NTx-mouse IgG-particle), then any anti-mouse antibody can be non-diffusively immobilized at zone 66. Any protein carrier can be used to conjugate to NTx, and the corresponding antibody (to the protein carrier) is then non-diffusively immobilized to zone 66.

Alternatively, any generic binding partner such as Protein A, Protein G or Protein A/G (e.g., obtained from Pierce) can be non-diffusively immobilized at zone 66 as long as it binds the particle-antigen conjugate. Lectins can also be immobilized at zone 66, provided that the particle-antigen conjugate can be bound at this zone.

Biotin, avidin or streptavidin can be conjugated to the particle-linked antigen, and the complementary binding partner can then be non-diffusively immobilized in zone 66. For example, if biotin is conjugated to the particle along with the antigen (in this case NTx), thus producing a biotin-particle-NTx conjugate, then avidin or streptavidin can be non-diffusively immobilized in zone 66.

Any non-human antigen, including proteins or small molecules such as dinitrophenol, known dinitrophenyl group-containing molecules or fluorescein, can be co-conjugated with NTx to the particle, and the complementary antibody can be immobilized in zone 66, the requirement being that the particle conjugate that is not bound in zone 64 is substantially all captured (bound) in zone 66 in the assay.

In the assay operation, the sample is introduced to the proximal end of the assay strip in the area of the particle-linked antigen conjugate zone 62. The sample can be directly applied, or alternatively, it can be pre-treated, filtered, and/or separated as described above. The fluid sample (which may contain antigen, in this case NTx) then reconstitutes the particle-antigen (particle-protein-NTx) conjugate, and the mixture of particle-protein-NTx and free analyte (NTx) moves via capillary migration or bibulous wicking action from zone 62 to zone 64, where the free antigen and particle-conjugated antigen compete for non-diffusively immobilized antibody. The antigen-particle conjugate that does not bind to zone 64 migrates to zone 66 and is substantially all bound by the non-diffusively immobilized member of the specific binding pair immobilized at this site.

At zero sample analyte/antigen concentration, the particle-antigen conjugate is mostly bound in zone 64, resulting in a dark color being produced in this zone. At very high sample analyte/antigen concentrations, the analyte/antigen occupies most of the binding sites of zone 64, causing the particle-linked conjugate to move past zone 64 to zone 66, where it is substantially all bound. Intermediate concentrations of sample analyte/antigen result in a predictable response relative to the bound particle signals in zones 64 and 66.

In general, low analyte/antigen concentrations result in high signal in zone 64 and low signal in zone 66. As sample analyte/antigen concentration increases, the signal in zone 64 becomes progressively smaller, and the signal in zone 66 becomes correspondingly higher. The total signal or detectable response (i.e., the sum of the signals from zones 64 and 66), remains substantially constant regardless of the analyte/antigen concentration (e.g., across the entire concentration range of from 0 to about 100 mM). This provides a reliable assay result and quality reference since the sum must stay within a specified range, otherwise an assay failure is indicated.

Assay calibration and sample quantitative measurement can be achieved using zone 64 alone, zone 66 alone or both zones 64 and 66. Under certain conditions, one test zone may produce better performance in a particular analyte/antigen concentration range, and another test zone may produce better performance in a different analyte/antigen concentration range. In this case, a hybrid calibration can be done that uses the optimal calibration range of each zone. Thus, the present two-test zone measurement provides substantial improvements over previously described methods.

The present test strip may be advantageously used in an instrument which reads the signals in zones 64 and 66. Thus, the indicator signals need not be visually detectable.

Figure 17:
FIG. 17 illustrates a side view of one embodiment of an assay strip suitable for use in a immunoassay.

FIG. 17 illustrates another embodiment of the present invention which is particularly useful for immunoassays. Similar in design to FIG. 3A, an additional reagent membrane layer is added between the metering layer and the original reagent layer. The additional reagent layer can contain diffusively or non-diffusively bound reagents which react with the sample as it proceeds toward the final reagent layer wherein the assay test results are displayed. For example, the NTx immunoassay can be arranged in this stacked configuration as opposed to the lateral configuration illustrated in FIGS. 15 and 16.

The present invention provides for multiple additional reagent layers preceding the final reagent layer. One test zone can also have a different number of reagent layers than the other test zone(s). The present invention is also not limited to distinct layers of porous material containing the reagents or any other chemical entity. A single porous material can be impregnated at different depths within the porous material with one or more layers of reagents or other chemicals to perform their designated function as the sample, or one of the sample's components, flows through the porous material.

Numerous modifications and variations of the present invention are possible in, light of the above teachings. It is therefore to be understood that within the scope of the appended claims, the invention may be practiced otherwise than as specifically described herein.

What is claimed is:

1. A dry reagent lateral flow strip assay device for detecting two or more analytes in a test sample comprising:
   a) a sample application zone; and
   b) two or more test zones;
   wherein the sample application zone and the two or more test zones are in fluid communication with one another through a transport matrix; and wherein the transport matrix further comprises a lateral path along which the sample travels in a lateral direction, and a transverse path along which the sample travels in a direction transverse to said lateral path, said lateral path being in a two-dimensional plane and said transverse path being in a third dimensional plane so as to direct said test sample to said two or more test zones.

2. The assay device of claim 1 for performing general chemistry assays, wherein the two or more test zones are general chemistry reagent zones comprising at least one enzyme.

3. The assay device of claim 2, wherein the enzyme produces a reaction product when at least one of the analytes is present in the sample.

4. The assay device of claim 1, wherein the two or more analytes are general chemistry analytes selected from the group consisting of: creatine, creatinine, glucose, cholesterol, high density lipoprotein (HDL) cholesterol, N-telopeptide, low density lipoprotein (LDL) cholesterol, triglycerides and blood urea nitrogen (BUN).

5. The assay device of claim 1, wherein one of the at least two or more test zones is a general chemistry reagent zone, said general chemistry reagent zone further comprising an indicator.

6. The assay device of claim 5, wherein the indicator forms a detectable signal when at least one of the analytes is present in the sample.

7. The assay device of claim 1 for performing a binding assay, wherein the two or more test zones are binding member zones comprising at least one binding member.

8. The assay device of claim 7, wherein the binding member is an antibody.

9. The assay device of claim 8, wherein the antibody is immobilized in the binding member zone.

10. The assay device of claim 9, wherein the antibody is diffusively immobilized in the binding member zone.

11. The assay device of claim 9, wherein the antibody is non-diffusively immobilized in the binding member zone.

12. The assay device of claim 7, wherein at least one of the binding members forms a complex with at least one analyte.

13. The assay device of claim 7, wherein at least one of the binding member zones further comprises an indicator that forms a detectable signal when at least one of the analytes is present in the sample.

14. The assay device of claim 1, wherein the two or more analytes are selected from the group consisting of: antigens, antibodies, macromolecules, vitamins, lectins, carbohydrates, proteins, peptides, amino acids, hormones, steroids, therapeutic drugs, drugs of abuse, bacterium and viruses.

15. The assay device of claim 1, wherein the two or more analytes are haptens that form binding pairs with antibodies.

16. The assay device of claim 1, wherein the sample application zone further comprises a sample pad in fluid communication with the transport matrix.

17. The assay device of claim 16, further comprising a sample treatment pad in fluid communication with the transport matrix.

18. The assay device of claim 17, wherein the sample treatment pad comprises a quaternary ammonium derived membrane for trapping ascorbate and other anionic interferents.

19. The assay device of claim 16, further comprising a sample filter pad in fluid communication with the transport matrix for removing undesired contaminants from the sample.

20. The assay device of claim 16, wherein the sample pad removes large particulate debris from the sample.

21. The assay device of claim 16, wherein the sample pad adjusts the pH and ionic composition of the sample.

22. The assay device of claim 1, wherein the transport matrix is a porous material along which the sample travels laterally.

23. The assay device of claim 1, further comprising a metering layer between the transport matrix and the two or more test zones through which the sample spreads uniformly across the transport matrix.

24. The assay device of claim 1, further comprising a detection zone corresponding to each test zone.

25. The assay device of claim 1, further comprising a sample treatment pad overlapping said transport matrix, a first layer also overlapping said transport matrix, and a second layer overlapping said first layer.

26. The assay device of claim 25, wherein said two or more test zones are located in said second layer.

27. A dry reagent lateral flow strip assay device for detecting two or more analytes in a test sample comprising:
 a) a sample application zone; and
 b) two or more test zones;
 wherein the sample application zone and the two or more test zones are in fluid communication with one another through a transport matrix;
 wherein said sample application zone further includes a sample pad and a sample treatment pad in fluid communication with said transport matrix;
 wherein said sample treatment pad comprises a quaternary ammonium derived membrane for trapping ascorbate and other anionic interferents; and
 wherein the transport matrix further comprises a lateral path along which the sample travels laterally, and a transverse path along which the sample travels transversely.

* * * * *

UNITED STATES PATENT AND TRADEMARK OFFICE
CERTIFICATE OF CORRECTION

PATENT NO. : 7,476,548 B2
APPLICATION NO. : 10/816230
DATED : January 13, 2009
INVENTOR(S) : Joel M. Blatt et al.

It is certified that error appears in the above-identified patent and that said Letters Patent is hereby corrected as shown below:

Title page, (54) Title "DRY REAGENT STRIP CONFIGURATION, COMPOSITION AND METHOD FOR MULTIPLE ANALYTE DETERMINATION" should read --DRY REAGENT STRIP CONFIGURATION AND SYSTEMS AND METHODS FOR MULTIPLE ANALYTE DETERMINATION--.

Title page, Abstract, line 2, "fluid is" should read --fluid are--.

Column 1, line 1, "DRY REAGENT STRIP CONFIGURATION, COMPOSITION AND METHOD FOR MULTIPLE ANALYTE DETERMINATION" should read --DRY REAGENT STRIP CONFIGURATION AND SYSTEMS AND METHODS FOR MULTIPLE ANALYTE DETERMINATION--.

Column 2, line 26, "15minutes" should read --15 minutes--.
Column 2, line 47, "According," should read --Accordingly,--.
Column 3, line 10, "seconds);" should read --seconds;--.
Column 3, line 22, "(mM)" should read --(mM))--.
Column 3, line 37, "mM" should read --mM)--.
Column 4, line 32, "to a analytic" should read --to analytic--.
Column 7, line 65, "which are" should read --which is--.
Column 9, line 66, "8hours" should read --8 hours--.
Column 10, line 1, "stripe" should read --strip--.
Column 10, line 5, "riot limited to," should read --not limited to--.
Column 10, line 20, "stripe" should read --strip--.
Column 11, line 7, "was ran" should read --run--.
Column 12, line 52, "ran" should read --run--.
Column 14, line 30, "besecured" should read --be secured--.
Column 14, line 60, "2seconds" should read --2 seconds--.
Column 15, line 24, "ofabout" should read --of about--.
Column 15, line 26, "layersmay" should read --layers may--.
Column 15, line 48, "width-." should read --width.--.
Column 16, line 65, "of0.45" should read --of 0.45--.
Column 20, line 39, "in, light" should read --in light--.

Signed and Sealed this

First Day of June, 2010

David J. Kappos
*Director of the United States Patent and Trademark Office*